United States Patent
Baiz et al.

(10) Patent No.: US 9,222,881 B2
(45) Date of Patent: Dec. 29, 2015

(54) VIBRATIONAL SPECTROSCOPY FOR QUANTITATIVE MEASUREMENT OF ANALYTES

(75) Inventors: Carlos R. Baiz, Cambridge, MA (US);
Kevin C. Jones, Cambridge, MA (US);
Andrei Tokmakoff, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 152 days.

(21) Appl. No.: 13/404,868

(22) Filed: Feb. 24, 2012

(65) Prior Publication Data

US 2013/0221222 A1 Aug. 29, 2013

(51) Int. Cl.
*G06F 19/10* (2011.01)
*G01N 21/35* (2014.01)
*G01N 21/63* (2006.01)
*G01N 21/3577* (2014.01)

(52) U.S. Cl.
CPC .............. *G01N 21/35* (2013.01); *G01N 21/636* (2013.01); *G06F 19/10* (2013.01); *G01N 21/3577* (2013.01); *G01N 2201/1293* (2013.01)

(58) Field of Classification Search
CPC ...................................................... G06F 19/10
USPC ...................................................... 250/339.1
See application file for complete search history.

(56) References Cited

U.S. PATENT DOCUMENTS

| | | | |
|---|---|---|---|
| 2003/0016358 A1 | 1/2003 | Nagashima et al. | |
| 2003/0157725 A1* | 8/2003 | Franzen et al. | 436/171 |
| 2007/0018103 A1 | 1/2007 | DeCamp et al. | |
| 2007/0152154 A1 | 7/2007 | DeCamp et al. | |
| 2009/0161092 A1 | 6/2009 | Zanni et al. | |

(Continued)

FOREIGN PATENT DOCUMENTS

| | | |
|---|---|---|
| JP | 2000275105 A | 10/2000 |
| JP | 2003194713 A | 7/2003 |

(Continued)

OTHER PUBLICATIONS

Khalil, et al., "Coherent 2D IR Spectroscopy: Molecular Structure and Dynamics in Solution", *J. Phys. Chem.*, 2003, 107:5258-5279.

(Continued)

*Primary Examiner* — Constantine Hannaher
*Assistant Examiner* — Hugh H Maupin
(74) *Attorney, Agent, or Firm* — McCarter & English, LLP

(57) ABSTRACT

The present invention relates to systems and methods for the determination of the secondary structure composition of proteins using coherent two-dimensional infrared (2DIR) spectroscopy of backbone amide I vibrations (1580-1720 $cm^{-1}$). Fractions of α-helix, β-sheet, and unassigned regions in globular proteins were determined by singular value decomposition using basis spectra from sixteen commercially-available proteins with known crystal structures. Preferred methods included removing each protein from the set and comparing the predicted composition against the crystal structure. The root-mean-squared (RMS) errors of the predicted secondary structure compositions were found to be 7.9% for α-helix, 5.5% for β-sheet, and 7.6% for unassigned regions. The structure analysis can also be performed using one-dimensional absorption spectra and the RMS errors are compared with those obtained from 2DIR.

85 Claims, 18 Drawing Sheets

(56) References Cited

U.S. PATENT DOCUMENTS

2010/0171952 A1    7/2010  DeFlores et al.
2014/0349337 A1*  11/2014  Dasari et al. .................. 435/40.5

FOREIGN PATENT DOCUMENTS

WO      WO-0050859   A1   8/2000
WO      WO-2009/075702 A2  6/2009

OTHER PUBLICATIONS

Selig, et al., "Inherently Phase-Stable Coherent 2D Spectroscopy Using Only Conventional Optics", *Optical Society of America*, 2008, pp. 1-3.

Xiong et al., "Signal enhancement and background cancellation in collinear two-dimensional spectroscopies", *Optics Letters*, 2008, 33(12): 1371-1373.

* cited by examiner

Distinguish different conformers or distributions of structures.

Analyze DNA or RNA structure: ssDNA Aptamers

VIBRATIONAL SPECTROSCOPY FOR QUANTITATIVE MEASUREMENT OF ANALYTES

STATEMENT REGARDING FEDERALLY SPONSORED RESEARCH OR DEVELOPMENT

This invention was made with government support under Grant No. CHE-0911107 awarded by the National Science Foundation. The government has certain rights in this invention.

BACKGROUND OF THE INVENTION

Modern structural biology seeks to establish a molecular understanding of biological function by exploring structure-function relationships in biomolecules. The mechanisms for protein folding, protein-protein interactions, ligand binding and catalysis are fundamentally linked to structure. Membrane proteins, in particular, drive key biological processes such as cell-signaling, and ion transport through the cell membrane. Despite the abundance, diversity, and biological importance of membrane proteins, relatively few crystal structures have been solved due to the difficulty in crystallizing the proteins. Modern tools such as cryo-electron-microscopy or x-ray crystallography enable detailed measurements of protein structure on multiple length-scales; however, structures are usually measured under non-biological conditions where key dynamic effects that lead to protein stability and function are not captured. Aside from NMR spectroscopy, most bio-analytical tools in use today are not sensitive to protein structure, heterogeneity, or conformational dynamics. Specific classes of proteins such as fibrous proteins, intrinsically disordered proteins, gels, amyloids, and aggregates, have been particularly difficult to characterize due to a lack of structural techniques available.

Infrared spectroscopy in the amide I region has been used to measure protein structure in solution. The vibrational modes in these regions involve primarily backbone C=O and N—H vibrations that are relatively sensitive to secondary structure and are largely free from the influence of side-chain absorptions. To date, however, most infrared measurements have offered either qualitative information or have required significant efforts to vibrationally isolate individual residues through isotope labeling. Attempts to extract structural information from amide-I and II absorption bands in proteins have relied on complex deconvolution and fitting to analyze largely featureless absorption bands. The results of these measurements are heavily dependent on the specific set of frequencies and fitting functions used, which greatly limits the usefulness of linear infrared spectroscopy as a structural tool.

SUMMARY OF THE INVENTION

The present invention relates to vibrational spectroscopy as a technique to measure structures of analytes. The systems and methods utilize the fact that secondary structures have specific signatures which allow for a quantitative decomposition of an analyte spectrum into combinations of different secondary-structure spectra. Preferred embodiments utilize multidimensional infrared spectral measurements to measure and analyze conformational structures at the molecular level. The present invention provides quantitative characteristics of analytes and dynamic properties of these analytes undergoing conformational change.

Various implementations of 2DIR have been devised in which excitation and detection frequencies have been measured either in the time or frequency domain. One method involves using a pair of two IR pulses to excite a sample and a third pulse to stimulate emission. The emitted signal is often detected in the frequency domain using a grating spectrometer, although time-domain detection has also been demonstrated. The two excitation pulses are delayed in time and the signal spectrum is often measured as a function of the time delay between these two pulses. A numerical Fourier-transform along the excitation time delay yields the excitation frequency. In order to produce a two-dimensional spectrum, the amplitude and phase of the emitted electric field must be measured. This is achieved either by using an external reference beam, or by using the third (detection) pulse as an internal reference. If the two excitation pulses are collinear, then the signal is emitted in the same direction as the detection pulse. However, if the excitation pulses are non-collinear, the signal is emitted in a background free direction.

In preferred embodiments of the present invention, the two excitation pulses are focused non-collinearly at the sample, and the emitted signal is overlapped with an external reference pulse at the detector. Different methods can be used to store, display and process data in accordance with the invention. The two (or more) axes used for spectral analysis can include excitation frequency versus detection frequency, time versus frequency, time versus time, etc. The pulses can be shaped to further modulate the conditions of a measurement.

Preferred embodiments of the invention provide for the quantitative measurement of different states of an analyte such as different isomeric structures or the different conformations of proteins or the rate of change of conformational structure undergoing dynamic changes, i.e. as a function of time.

The present invention provides a simple and reliable analysis to quantify the percentage of amino-acids in α-helix or β-sheet conformations of proteins in solution. Multidimensional spectroscopy has been developed as a technique to characterize complex systems in solution. In particular, coherent two-dimensional infrared (2DIR) spectroscopy has the ability to directly measure the structure, static disorder, conformational flexibility, and solvent exposure of residues within a protein. 2DIR spectroscopy can provide new insights into protein structure and heterogeneity, protein dynamics, protein-protein interactions and ligand binding. However, the amount of structural information extracted from 2DIR has remained largely qualitative, and in most cases the equilibrium structure of the protein under investigation is known a priori. The present invention utilizes the structural-sensitivity of 2DIR spectroscopy in order to develop a quantitative method to measure secondary structures of analytes.

Amide-I vibrations involve primarily combinations of backbone carbonyl stretches. The 'local' carbonyl stretches, corresponding to each individual amino acid linkage within the protein, form the basis for the delocalized normal modes. The frequencies of the normal modes are given by the frequencies of the local C=O stretches as well as the magnitude of the couplings between these local oscillators. Coupling patterns report on the secondary structure and conformational disorder of the residues: structured regions exhibit highly regular coupling patterns whereas disordered regions exhibit a random coupling pattern. Each oscillator within a particular secondary structure is coupled strongly to the other oscillators in the secondary structure giving rise delocalized normal modes. The frequency of the delocalized vibrations tends to separate into particular ranges: β-sheets exhibit two peaks near 1630 and 1680 $cm^{-1}$ whereas α-helices and unstructured regions appear near 1650 $cm^{-1}$. Despite the secondary structure-sensitivity of the peak frequencies, conformational disorder and solvent exposure render the absorption bands broad and largely featureless.

Analogous to NMR spectroscopy, a 2DIR spectrum can be interpreted as follows: the vibrations of the samples are first excited, or labeled, by a set of two infrared pulses, and after a certain waiting time, a third pulse stimulates the emission of the modes within the sample. The excitation frequency (horizontal axes) and a detection frequency (vertical) are then combined in a two-dimensional plot. Diagonal peaks are due to excitation and detection at the same frequencies, and cross peaks arise from excitation of one vibration, and detection of a different vibration. Cross peaks are observed only if two vibrations share common atoms, or in this context, common residues. 2DIR spectroscopy offers enhanced structure-sensitivity by spreading the spectral content onto two frequency axes. Cross peaks are usually observed if two vibrational modes are coupled (i.e. if the two vibrations share common residues). For example, in the case of β-sheets, off-diagonal features are observed between the two main peaks at 1630 and 1680 cm⁻ with a corresponding cross peak, however negligible cross peaks are observed between α-helix and β-sheet vibrations since these involve different residues. Further analysis of the main spectral features associated with each secondary structure is provided in the discussion section below.

Systems in accordance with preferred embodiments of the invention include a spectral data measurement system and a data processing system that is programmed to analyze spectral data for the quantitative measurement and analysis of analytes. An electronic display can display the analyzed data which can also be stored in electronic memory and/or transmitted via private or public computer networks. The system uses a light source system, an optical system for generating light pulses that illuminate the analyte to be measured and a detector system that detects light from the analyte in response to the illuminating light. Motarized stages can be used to control positioning of optical elements within the optical system for light pulse control and shaping.

DETAILED DESCRIPTION OF THE INVENTION

Figure 1A:
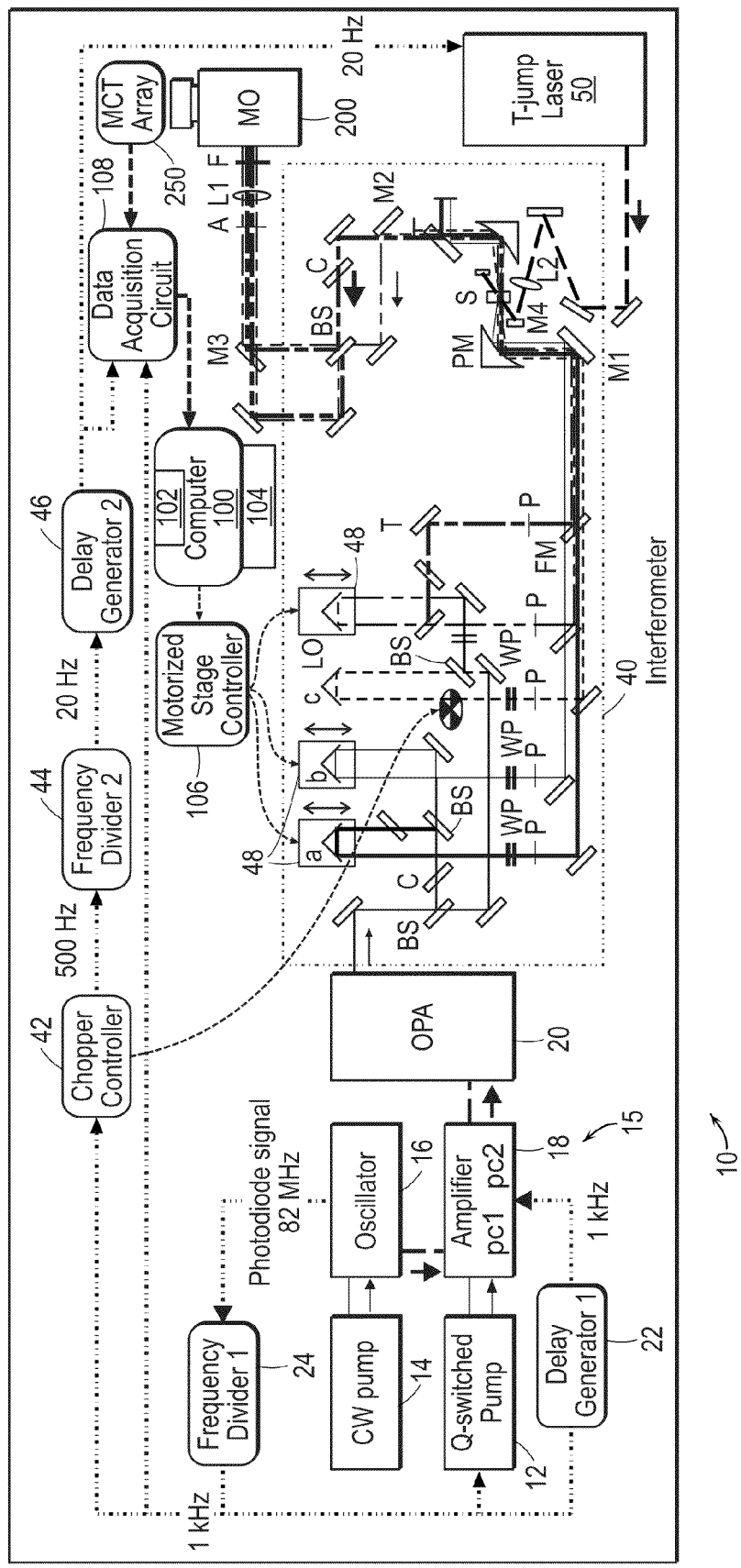
FIG. 1A illustrates a system for multidimensional IR spectral measurements in accordance with preferred embodiments of the invention including detector, controller, and flowchart of the frequency division; the rectangular boxes with sharp corners represent lasers and those with rounded corners represent electronic devices including a computer and a detector. The flow of the electronic triggers is represented by the dashed arrows connecting the electronic component: BS (orange rectangle bar), beam splitter; C (green rectangle bar), compensator; LO, local oscillator; T, tracer; P (–), polarizer; WP (=), half-wave plate; FM, flipper mirror; PM, parabolic mirror; S, sample; A, analyzer; F, low-pass filter, L1, CaF$_2$ lens (f=11 cm); L2, BK7 lens (f=10 cm); MO, monochromator.

The two-dimensional spectrometer system 10 is illustrated in FIG. 1A. The system provides for the acquisition of 2D IR spectra and related dispersed vibrational echo (DVE) spectra, the synchronization of femtosecond 15 and T-jump laser 50 systems, and the acquisition of transient 2D IR and DVE spectra. The optical components used to generate and detect the nonlinear signal is shown in FIG. 1A. A Ti:sapphire oscillator system 14, 16 (Tsunami, Spectra-Physics) is used to obtain an initial femtosecond pulse, which is amplified by a regenerative amplifier 18 (Spitfire, Spectra-Physics). The amplified pulse pumps an optical parametric amplifier 20 (OPA). The signal and idler fields are focused onto the AgGaS$_2$ crystal (C) to generate a 90 fs [full width at half maximum] (FWHM) mid-IR pulse centered at 6 um (FWHM 160 cm⁻¹) by difference frequency mixing. A single IR pulse is divided into four identical pulses by 4-mm-thick 50:50 ZnSe beam splitters (BS) (BS1516Z50050S, Rocky Mountain Instrument). ZnSe compensators (W11012Z550BA2+, Rocky Mountain Instrument) are used to maintain the same chirp character between the transmitted and reflected pulses. Each femtosecond pulse travels to and is reflected back by a retroreflector 48 (3 in. in diameter, PLX). The positions of the retroreflectors for beams a and b, and LO (tracer) are controlled by the motorized linear stages adjusted by stage controller 106 (ANT-50L, Aerotech) to adjust the relative delay between pulses with a resolution of 10 nm (0.067 fs), an accuracy of 300 nm (2 fs), and repeatability of 50 nm (0.33 fs). Beam c is chopped at 500 Hz. The fourth beam is further split into the local oscillator (LO) and the tracer (T). The tracer beam is only sent to the sample by the flipper mirror (FM) when the pump-probe signal is collected. The polarization of each beam is controlled by a wire-grid polarizer (P) (IGP229-25HER-0921, Molectron) and $MgF_2$ half-wave plate (WP) (MWPMFA2-22-6M, Karl Lambrecht Corp.) pair. The energy in each of the identical pulses a, b, and c after the polarizer and half-wave plate pair is 0.15 µJ, for example. All beams are focused onto the sample (S) by a gold-coated off-axis (90% angle) parabolic mirror (PM) (3 in. in diameter, f=10 cm, A8037-308, Janos Technology) within the spot size of 100-110 µm in diameter at 90% transmission. The samples were placed in a temperature-controlled brass cell consisting of two 1-mm-thick and 1-in.-diam $CaF_2$ windows separated by a 50 µm thick Teflon spacer. The temperature of the cell can be regulated to ±0.1° C. by a circulating water bath. The quoted temperatures are those measured on the $CaF_2$ window by a thermocouple.

A preferred embodiment of the invention relates to the measurement of conformational structure of proteins. Transient 2D IR spectrometer provide for direct probing of protein unfolding over time scales from −2 ns to 50 ms following a Tjump. Synchronization of the femtosecond IR laser system and T-jump laser with minimal timing error relies on division of the stable reference clock signal (82 MHz) from the Ti-:sapphire oscillator down to 1 kHz and 20 Hz. Control of the time delay is provided to within 2 ns accuracy. The reduced repetition rate of the T-jump laser implies a longer data collection time. To overcome this difficulty, 2D IR spectra are obtained by undersampling the data acquisition points by a factor of 3.5. For an improved signal-to-noise ratio, also perform a balanced heterodyne detection of the nonlinear signal with a dual stripe array detector. The T-jump induced phase jitter in heterodyne detection is suppressed by propagating the local oscillator field through the T-jump region of the sample.

The three beams (a, b, and c) and the tracer propagate parallel to each other centered at the four corners of the 1 inch square box before being focused. The nonlinear signal field is generated in the wave-vector-matched direction $k_s=k_a+k_b+k_c$, ideally the same direction as the tracer. The LO enters the sample between the tracer and beam c. A time delay of 35 ps between the LO and three beams at the focal point on the sample ensures that the LO is separated from the three pulses by much longer than the amide I vibrational lifetime, but is much shorter than the T-jump pulse width. It therefore does not generate nonlinear signals. However, the LO experiences the same density perturbations in the sample as the other pulses as the probe beam does as pump beam in pump-probe spectroscopy. (Therefore, T-jump 2D IR spectroscopy will be directly applicable to another kind of 2D IR spectroscopy based on pump-probe spectroscopy.) The LO is overlapped temporally with the third order signal at the array detector 250.

After passing through the sample cell, the LO and the third order signal are allowed to propagate where beams a, b and c are masked. The LO is combined with the signal on either side of a 50:50 beam splitter after being picked off by M2. The reflected third order signal and transmitted LO pair (solid lines) are focused onto the upper stripe of the dual stripe (2×64) array mercury cadmium telluride (HgCdTe) (MCT) detector 250 (IR-0144, Infrared Systems Development) after being dispersed by a 190 mm monochromator (Triax 190, Jobin Yvon) with a 40 lines/mm grating. The other pair (dashed lines) propagates over the mirror (M3) and is focused onto the lower stripe. The analyzer (A) determines the polarization of the third order signal and the low-pass filter (F) removes the scattered T-jump pulse. A $CaF_2$ lens (L1, f=11 cm) focuses the third order signal and LO pairs onto the slit (0.2 mm) of the monochromator 200.

A data acquisition circuit 108 can be used for initial data processing before the spectral data is transmitted to data processor or computer for processing and display on the electronic display 102 and storage in memory 104. The computer can also be used to control system operations, such as motarized stage controller 106 and light sources. Delay generator circuits 22, 46, frequency dividers 24, 44 and chapper controller 42 are used to regulate pulse timing.

2D IR data were taken either in the parallel (ZZZZ) or in the crossed (ZZYY) polarization geometry. Rephasing ($k_s=k_1+k_2+k_3\equiv k_R$) and nonrephasing ($k_s=k_1-k_2+k_3\equiv k_m$) spectra are NR, obtained for $\tau_2=100$ fs by altering the time sequence of the $k_a$ and $k_b$ pulses. Dispersed heterodyned signals are collected onto the array detector with a spectral resolution of −4 cm$^{-1}$ in the $\omega_3$ dimension. To reduce data acquisition time, undersample the data as a function of $\tau_1$ in 14 fs steps from 0 to 2.1 ps for the rephasing and from 0 to 1.2 ps for the nonrephasing configurations, respectively. A Fourier transform of the $\tau_1$ axis yields the individual 2D rephasing and nonrephasing spectra, and the sum of these gives the absorptive 2D IR correlation spectrum. The actual frequency $\omega_1$ for the data collected by undersampling is obtained by reflecting the transformed frequency ($\omega_{1u}$) to the Nyquist frequency ($\omega_N$) as $$\omega_1=2\omega_N-\omega_{1u} \quad (1)$$

Figure 1B:
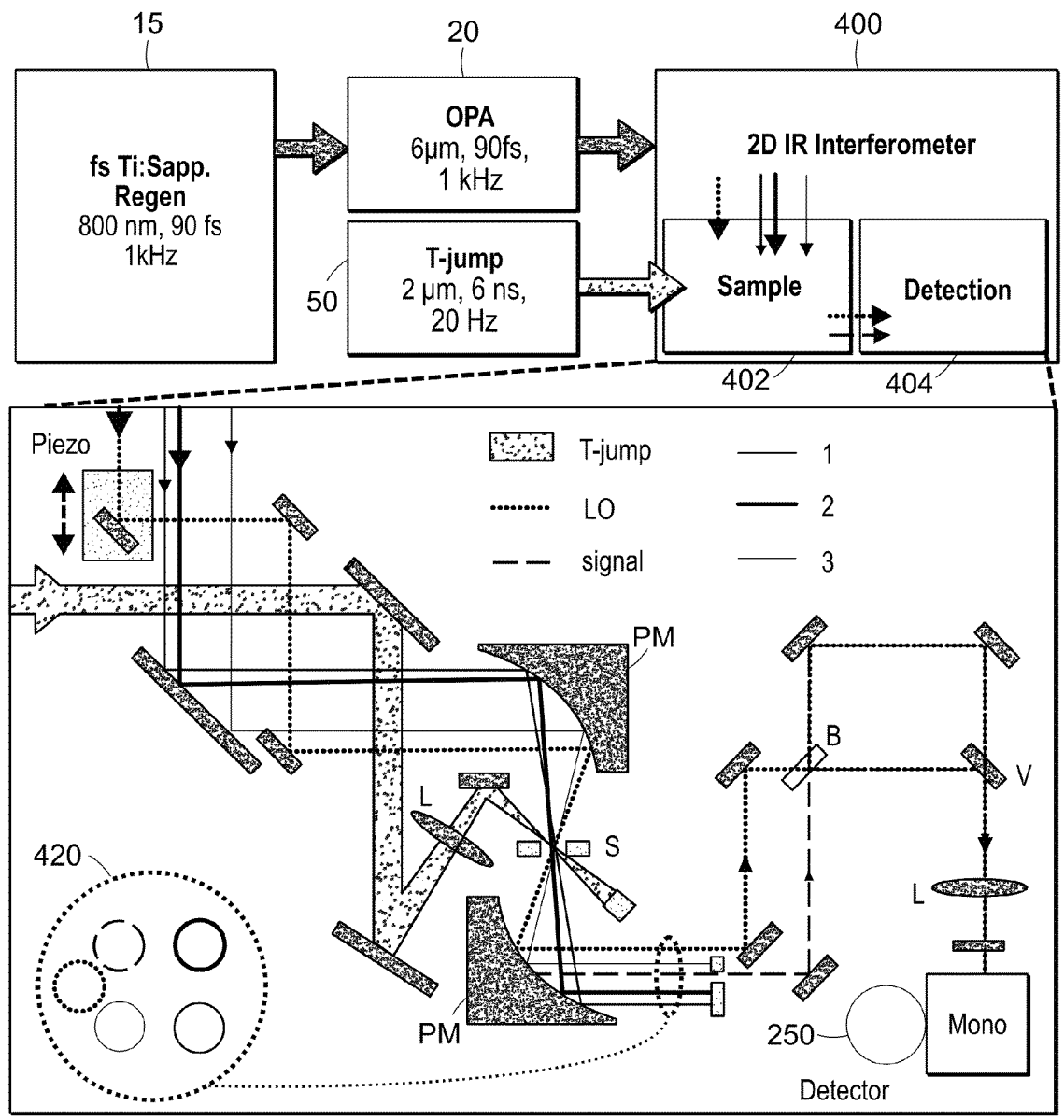
FIG. 1B illustrates another preferred embodiment of a spectrometer in accordance with the invention.

The resolution in the $\omega_1$ dimension after Fourier transformation is 0.5 cm$^{-1}$. FIG. 1B illustrates another preferred embodiment utilizing three IR beams to generate a third order signal in the sample. The LO beam delay is stopped using the piezo controlled stage.

The system 400 that illuminates the sample (S) 402 and detects 404 the transmitted signal is enlarged and shows the beam geometry in the sectional view 420. The mirrors PM are symmetric about the sample so that noncolinear beams converge on the sample and subsequently separated for detection.

Additional details regarding systems and methods used in connection with preferred embodiments of the invention are described in International Application No. PCT/US2008/010460 filed Sep. 8, 2008, claiming priority to U.S. Application No. 60/967,889 filed on Sep. 7, 2007 and further corresponding to U.S. application Ser. No. 12/676,536 filed Mar. 4, 2010, the entire contents of the above application being incorporated herein by reference.

Figure 2:
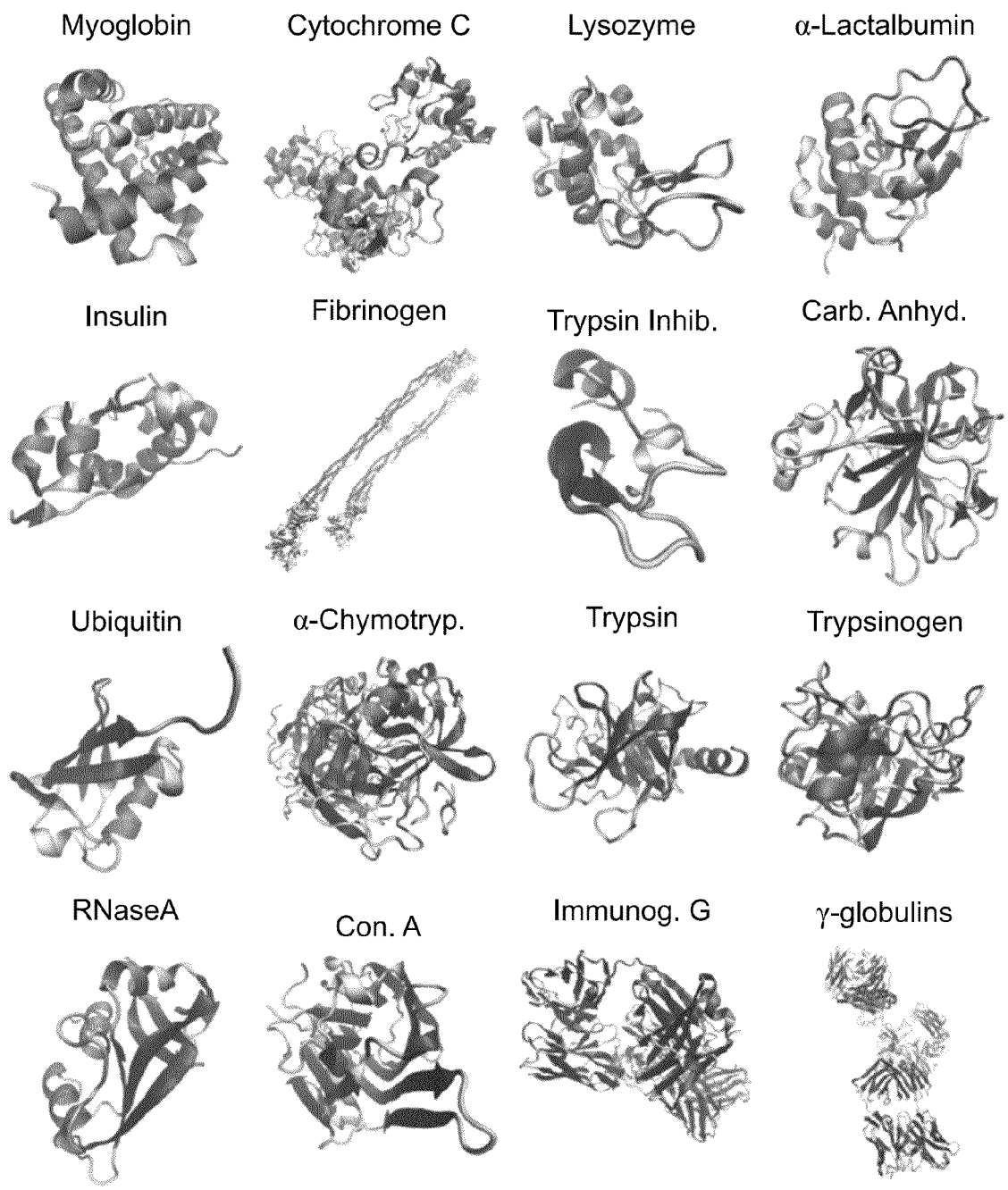
FIG. 2 PDB Structures of the proteins used for SVD analysis. α-helix and β-sheet structures are colored in red and blue respectively; The proteins are arranged in order of increasing β-sheet contents as calculated by the DSSP program.

The set of proteins used in connection with the present invention were FIG. 2 selected to span a wide variety of structures ranging from mainly α-helical proteins (Myoglobin) to mainly β-sheet proteins (γ-globulins). The solubility, robustness, and commercial availability of each protein were also considered. All samples were obtained from Sigma-Aldrich and were used without further purification. The samples were hydrogen/deuterium exchanged in $D_2O$ (Cambridge Isotopes, Andover Mass.) at 60° C. for 1 hour, and lyophilized at −210° C. Solid protein samples were stored at −20° C. to prevent degradation. The proteins were then redissolved in pure $D_2O$ at neutral pH* to a final concentration of 20 mg/ml. Fibrigonen, Immunoglobulin G and Insulin samples were dissolved in pH*=2 DCl solution. The solutions were placed in a temperature-controlled sample cell equipped with two $CaF_2$ windows and a 50 µm Teflon spacer. Experiments were carried out at 25° C.

The x-ray structure of each protein was obtained from the Brookhaven Protein Databank (PDB) and the secondary structure assignment was calculated with the DSSP program. DSSP uses the atomic coordinates and hydrogen-bonding patterns to assign each residue to the following structural elements: β-bridge, extended β-strand, 3-10 helix, α-helix, hydrogen bonded turns, and bends. For SVD analysis we combined the β-bridge and extended β-strand into a single structural element β-sheet, and combined the α-helix and 3-10 helix residues into an effective α-helix, all other residues were labeled unassigned.

Singular value decomposition (SVD) is a matrix-diagonalization technique used to extract the principal spectral component spectra that describe the dataset. Within this method a matrix of spectra M, is decomposed into three matrices such that, $$M = USV^T, \quad (2)$$

where the superscript T indicates a transpose of V. The SVD process is analogous to eigenvalue decomposition: Columnwise the matrix U contains a set of orthogonal basis spectra or SVD components, row-wise V contains the set of coefficients associated with the projection of each input spectrum (M) onto the individual basis spectra (U) and S is a diagonal matrix containing a set of weighting coefficients indicating the relative contribution of each basis vector in U to the input data set M. For preferred embodiments, FTIR spectra are input as one-dimensional arrays (vectors) where each entry corresponds to the absorbance at different frequencies, for example in the amide I region from 1580 to 1720 cm$^{-1}$. Two-dimensional spectra (in this sample, in the 1580 to 1720 cm$^{-1}$ cm region) are likewise column-wise reshaped into one dimensional arrays. In the 2DIR example the size of the matrices are as follows: M=7396×15, U=15×7396, S=V=15×15

Some of the U columns, V columns, and S diagonal values are zero or near zero. We discard these components and only keep the nonzero parts. As a result of this rejection, S becomes a square, invertible matrix.

If we assume that the protein spectra, M, are the linear combination of the secondary structure spectra weighted by their content, then we can decompose the spectra into:

$$\Sigma P^1 = M \quad (3)$$

where $\Sigma = \{m^{(\beta)}, m^{(\alpha)}, m^{(una)}\}$ and $P = \{p^{(\beta)}, p^{(\alpha)}, p^{(una)}\}$. The columns of Σ are the pure spectra of a β-sheet, α-helix, and unassigned structure, respectively. The columns of P contain the fraction of residues per protein in the β-sheet, α-helix, and unassigned conformation calculated using the DSSP program.

To transform the SVD results from equation (2) into the spectra and fractions in equation (3), we insert $XX^{-1} = I$ into equation (1):

$$M = USXX^{-1}V^T. \quad (4)$$

and solve for $X^{-1}$ such that:

$$X^{-1}V^T = P^T. \quad (5)$$

can then be inverted and multiplied to give Σ:

$$USX = \Sigma. \quad (6)$$

To assign the secondary structure $P^{(u)} = \{p^{(\beta)}(u), p^{(\alpha)}(u), p^{(una)}(u)\}$ of an "unknown" spectrum $m^{(u)}$, we solve the equation:

$$\Sigma(P^{(u)})^T = m^{(u)}. \quad (7)$$

Substitution of previous equations allows us to solve for $P^{(u)}$ with:

$$P^{(u)} = P^T V S^{-1} U^T m^{(u)}. \quad (8)$$

The SVD procedure is cross-validated for each sample by removing a specific spectrum from the initial set, building an SVD basis with the remaining spectra, and using the removed spectrum as the unknown. Finally the predicted percentage of secondary structure is compared with the percentage computed from the PDB structure.

Figure 3:
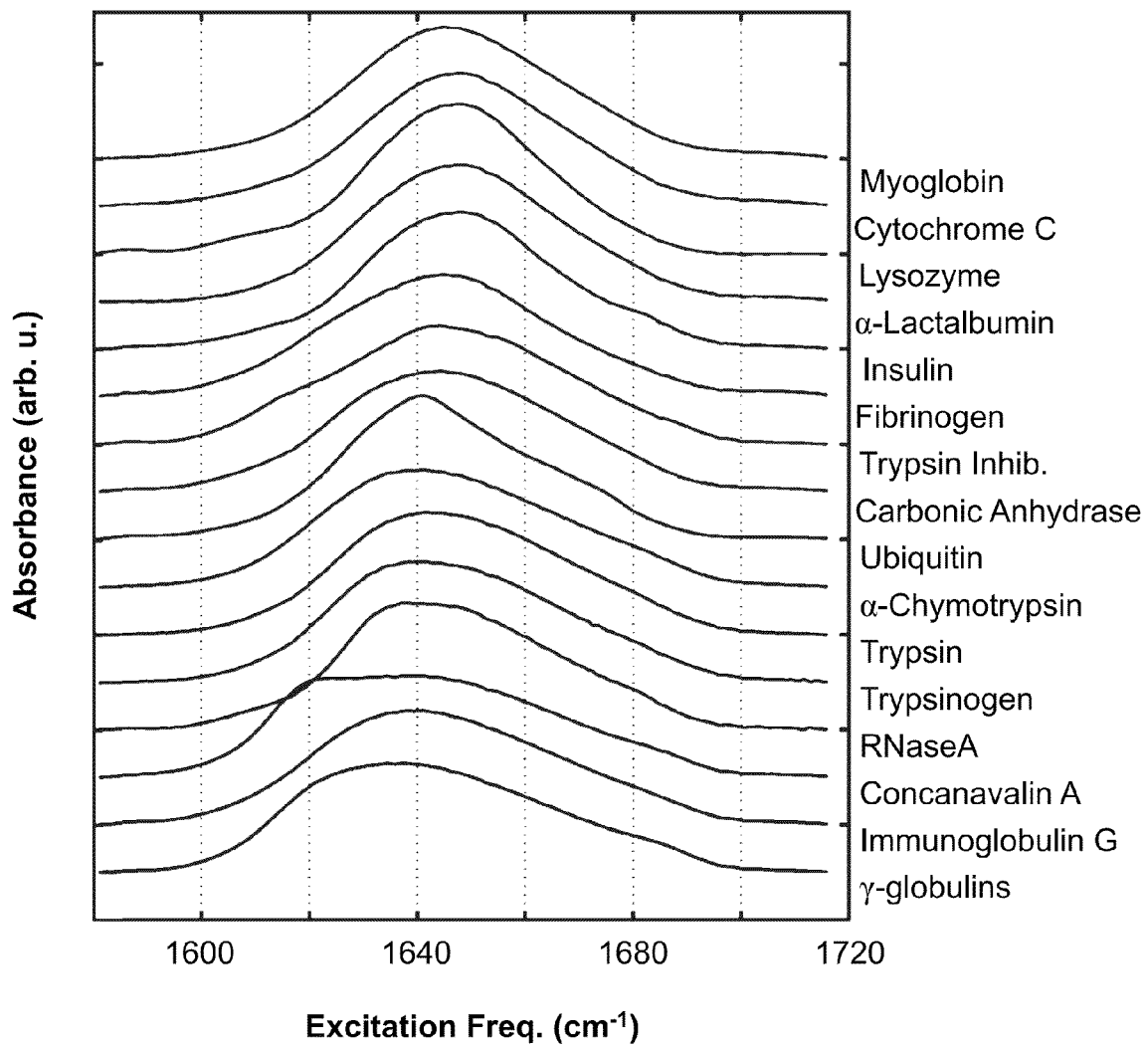
FIG. 3 illustrates amide-I linear absorption spectra in which peaks are normalized to the area in the 1580 to 1720 cm⁻¹ and vertically offset for clarity.
Figure 4:
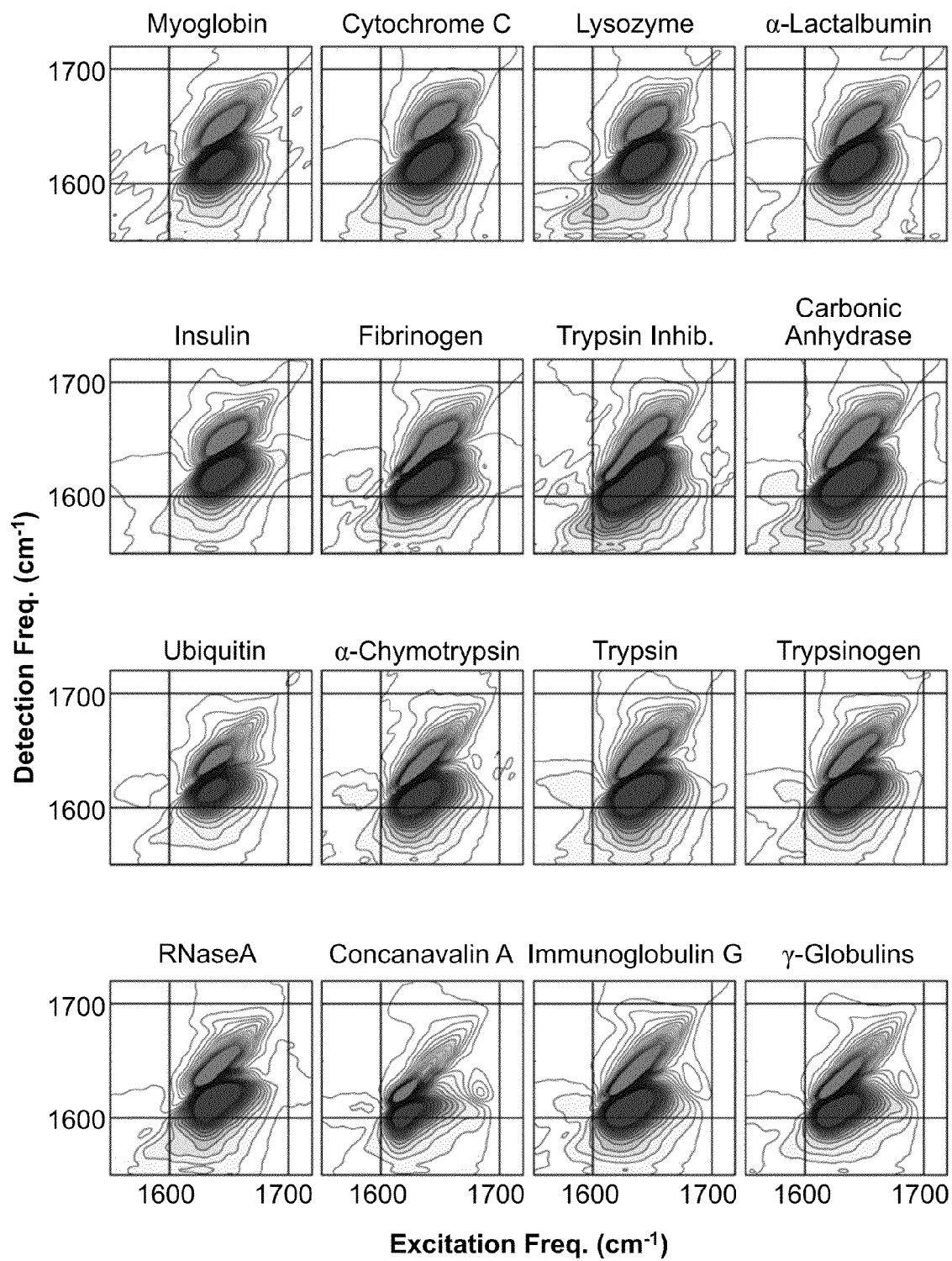
FIG. 4 Correlation 2DIR spectra of the proteins acquired in the perpendicular polarization geometry. Contours are plotted from +/−50% of the maximum amplitude in 4% intervals and spectra are arranged in order of increasing β-sheet content (see FIG. 2)

Measured IR absorption and 2DIR spectra are shown in FIGS. 3 and 4 respectively. Qualitatively, absorption spectra associated with primarily α-helical proteins are characterized by a single band centered near 1650 cm$^{-1}$ with an approximate diagonal width of 50 cm$^{-1}$, while proteins composed of primarily β-sheet show two peaks centered near 1620 and 1680 cm$^{-1}$ resulting from vibrations whose main transition dipoles lie perpendicular and parallel to the β-strands respectively. The amplitude ratio of $v_{parallel}$ to $v_{perp}$ reports on the size of the β-sheet. Described herein is the analysis to the total contents of α-helix and β-sheet which can be applied to other structures. 2DIR spectroscopy is sensitive to the size and shape of secondary structures; however a larger and more diverse basis set would be required for such analysis. Mixed α/β proteins show a combination of the features associated with helix, sheet and unstructured regions where the relative contributions of the individual features depends on the fraction of residues that compose each secondary structure. Peaks assigned to unstructured regions are centered near 1640 cm$^{-1}$ and thus tend to overlap with the α-helix peaks. This overlap increases the difficulty of unambiguously assigning α-helix and unstructured conformations in proteins. In general, diagonal linewidths report on the static heterogeneity (disorder) of the amide-I frequencies whereas the anti-diagonal linewidths report on the sub-picosecond dynamic fluctuations that are a result of protein-solvent interactions; and the ratio of diagonal to anti-diagonal linewidth serves as a measure of structural rigidity and solvent exposure. In this context it should be pointed out that since vibrations are highly delocalized residue-level resolution is often obtained through isotope labeling.

Figure 5:
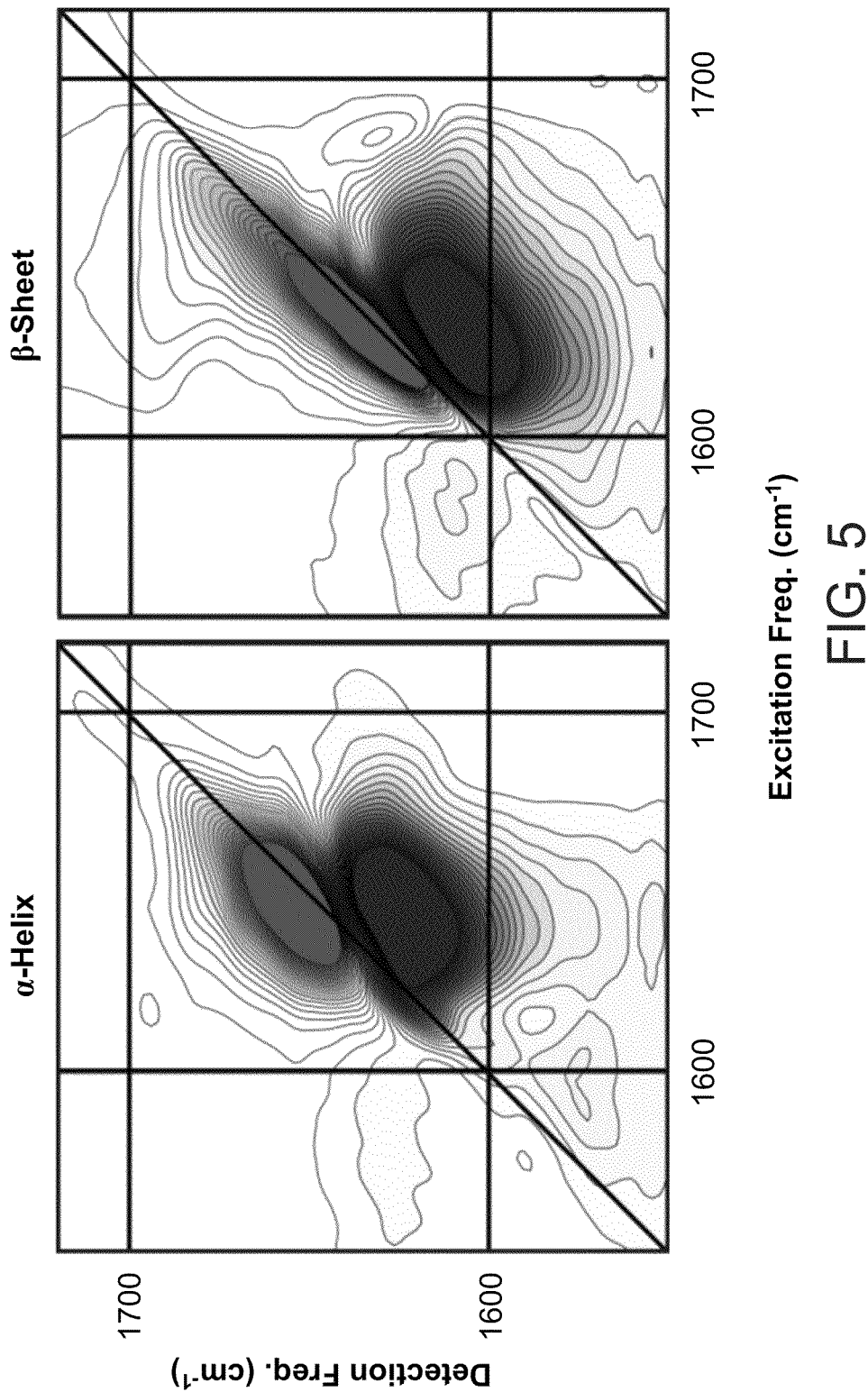
FIG. 5 includes SVD basis spectra wherein contours are plotted from +/−50% of the maximum amplitude in 4% intervals and spectra are arranged in order of increasing β-sheet content (see FIG. 2)

Once spectra are decomposed by SVD analysis and structure vectors are computed (eq. 3), it is informative to reconstruct the 2DIR spectra corresponding to purely α-helix, β-sheet, and unassigned components (eq. 6). FIG. 5 below shows the reconstructed SVD spectra; the α-helix spectrum shows a single round peak centered at 1650 cm$^{-1}$ whereas the β-sheet spectrum exhibits two peaks near 1630 and 1670 cm$^{-1}$ with the corresponding cross-peaks, giving the spectrum a characteristic "Z-shape" associated with primarily β-sheet proteins. SVD spectra are in agreement with our spectral assignment described in the previous section as well as with experimental and simulated spectra of idealized structures published previously. The component spectrum associated with the unassigned structures features a peak centered near 1640 cm$^{-1}$ with a distinct diagonal elongation due to the disorder associated with unstructured regions. Compared to spectra of unstructured proteins, the unassigned SVD spectrum shows a somewhat more pronounced diagonal elongation. In addition, a horizontal ridge near $\omega_{deletion} = 1680$ cm$^{-1}$ characteristic of β-sheet spectra is observed, indicating that the unassigned peak contains a small amount of β-sheet character, and may suggest that crystal structures underestimate the amount of β-sheet present in solution. This effect can contribute to the uncertainty in predicting secondary structure compositions by SVD analysis.

Figure 6:
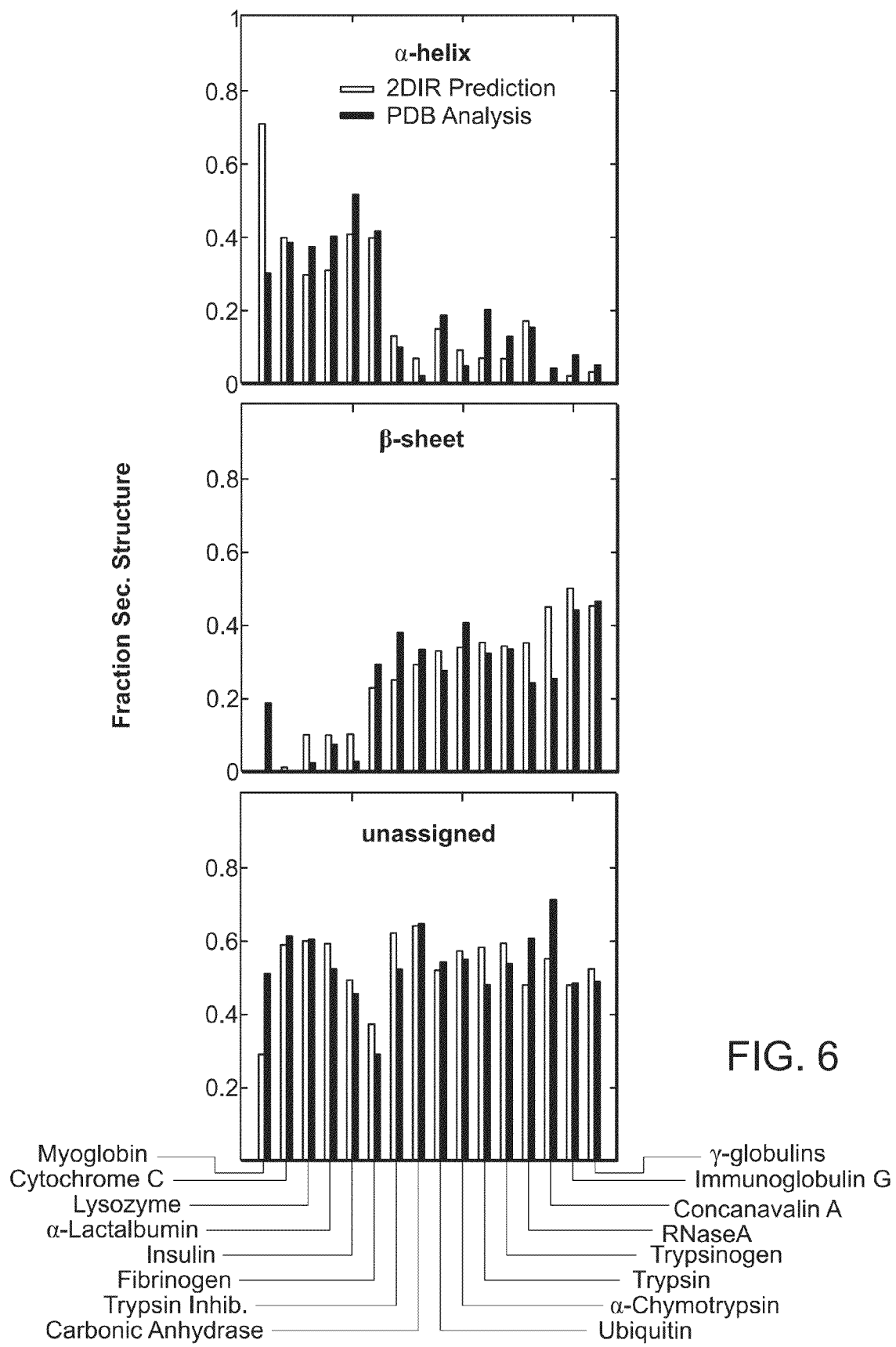
FIG. 6 Comparison between amount of secondary structure predicted by SVD analysis of the 2DIR spectra and the amount extracted from the x-ray structures using the DSSP program.

The SVD method is validated by removing each protein from the initial set, creating an SVD basis with the remaining structures, and using the new basis to analyze the "unknown" structure. FIG. 6 shows the fraction of each secondary structure predicted from SVD analysis along with the fractions obtained from the x-ray structure. Overall there is an excellent correlation between the predicted structures in solution with the compositions derived from the crystal structure. Not surprisingly the largest error is observed in Myoglobin where the protein lies outside of the conformational space spanned by the SVD basis set. Myoglobin was therefore removed from the root-mean-squared error calculation in this example. The expected result would be to see a large error for γ-globulins since this structure lies at the opposite extreme of the conformational space sampled by the SVD basis set, however the error is small, due to the fact that other proteins in the set such as Immunoglobulin G have a similar structure. The root-mean-squared errors in comparing the SVD prediction with the x-ray structure are 7.9, 5.5, and 7.6% for α-helix, β-sheet, and unstructured components respectively. Naturally, the β-sheet component is the most distinct and thus the errors in predicting the β-sheet structure are smaller.

Distinguishing between α-helices and unstructured regions has remained challenging for amide-I infrared spectroscopy as both peaks appear in the same region of the spectrum. As shown in FIG. 5, the two structures can be distinguished by the ratio of diagonal to anti-diagonal linewidths, making 2DIR a more sensitive probe of structure. For comparison, SVD decomposition using the FTIR spectra was performed. The RMS errors obtained for an FTIR-derived SVD basis are: 19.5, 8.3 and 21.5% respectively. This comparison highlights the structural-sensitivity gain associated with projecting the spectral information onto two frequency axes and measuring the diagonal as well as the anti-diagonal linewidths. It is important to point out that, unlike FTIR spectroscopy, 2DIR spectra not affected by small changes of the $H_2O$ background as the non-linear interactions largely suppress the broad background signal. Incomplete background subtraction, one of the largest sources of error in FTIR spectroscopy, has negligible effects on the 2DIR spectra.

Circular dichroism (CD) spectroscopy is a method to determine conformation and conformational changes of proteins in solution. Although the light-matter interactions of amide-I IR spectroscopy and ultraviolet dichroism spectroscopy are quite different, both methods measure the structure of the backbone of proteins by exciting transitions that are delocalized over the amide-I units and where the local structure of the units affects the absorption frequencies and intensities. The errors associated with secondary structure determination by 2DIR are comparable to those obtained from circular dichroism where the spectra are assumed to be a linear combination of the individual structure-spectra. These RMSE values are: 9% α-helix, 12% anti-parallel β-sheet, 8% parallel β-sheet, 7% β-turn, and 9% unassigned. These results show that 2DIR spectroscopy is a viable alternative to CD spectroscopy with the added advantage of ultrafast time resolution and the ability to isotope-label individual residues for increased structural resolution.

The observed (~8%) errors between structure determination techniques in solution compared to crystal structure likely reflect, in part, on the structural heterogeneity and the inherent differences in structure that are induced upon crystallization. Water can play a central role in maintaining the balance between entropic and enthalpic contributions that determine the structure and conformational flexibility needed for protein function.

Another source of error in measurement stems from the SVD basis itself. The SVD basis must reflect the region of conformational space of the unknown protein to be analyzed. For example, constructing a basis set of purely β-sheet proteins and using such basis to analyze an α-helical protein would likely result in a large error. A particularly large basis set is unlikely to capture the structural details of an individual proteins and therefore likely to produce an averaged-out measure of structure. To circumvent this limitation, it may be possible to perform a multi-level SVD analysis where the protein is initially screened using a large basis set, and based on the initial results the SVD basis is then further refined to include only proteins that are similar in structure to the unknown protein. However such analysis would be susceptible to errors in biasing the basis set towards a particular structure that may not accurately reflect the structure of the unknown protein.

Computational models and symmetry considerations for idealized β-sheets suggest that 2DIR spectroscopy is sensitive to the size and type of β-structure. To date a systematic measurement of pure β-sheet proteins has not been carried out. More generally, quantifying the spectral signatures of various structural motifs, with particular attention to heterogeneity and site disorder, will further enhance the capabilities of 2DIR spectroscopy as a structural technique.

Thus, preferred embodiments provide systems and methods to measure protein structure in solution based on ultrafast two-dimensional infrared spectroscopy. Spectra are analyzed by singular-value decomposition, a analysis technique that is not affected by the subjectivity of phenomenological fitting models. The model was tested on a set of sixteen commercially-available globular proteins with well-defined structures. The root-mean-squared errors compared to the crystal structures are 7.9, 5.5, and 7.6% for α-helix, β-sheet, and unstructured components respectively. The results show that 2DIR spectroscopy is capable of quantitative structure determination on stock proteins without the need for labeling. The key advantage, however, of 2DIR spectroscopy lies in its picosecond time resolution and ability to spread spectral information over two axes by correlating pump and probe energies. Combined with a laser-induced temperature-jump the method can be used to determine protein folding/unfolding pathways in solution and expand the current understanding of the structural-changes associated with protein folding and function.

Quantify secondary structures at additional features or characteristics such as the type of local hydrogen bond registry or nanometer scale structures, break down beta-sheets into parallel, antiparallel, beta-barrel, cross-beta-strand structures and/or identify alpha helices using right handed vs. left-handed configuration or α-helix vs 3/10 helix. Additional characteristics include beta-hairpin and beta-alpha-beta.

Quantitative information such as the size of structures (how many strands in a sheet, how long is each helix) can also be measured.

Further preferred embodiments provide for characterizing additional 3D conformational information such as super-secondary, tertiary, quaternary structures, twist and layers of sheets and helices, as well as the contacts present between sheets and helices. Additionally, the system can analyze contacts or formation of protein complexes. These methods can be combined with amide II (amide I-II) or with hydrogen/deuterium exchange to separate different hydration states of the protein (solvent exposed vs. buried) and identify conformational flexibility of different secondary structures.

Additional preferred embodiments provide for analysis of structural changes in time-dependent properties of proteins and other materials. Methods include applying to structural or kinetic information in any other protein vibrational lineshapes, or cross-peaks between different vibrational lineshapes. For example, ligand binding, protein aggregation, association/dissociation, and catalysis.

Preferred embodiments further comprise quantifying transient-structure of proteins with non-equilibrium 2DIR. These methods can be applied to analyze protein folding and function, including temperature-jump 2DIR, pH-jump, phototriggered ion release, and 2DIR spectroelectrochemistry (oxidation states).

These methods apply to different samples including membrane proteins, fibers, gels, and insoluble proteins. These can also be used for analysis of DNA and RNA, such as Watson-Crick base pairing: A-DNA, B-DNA, Z-DNA, G-quartets, RNA Structure and fluctuations, and RNA Ligand binding/Ion binding.

These methods provide for separating (bio) chemical mixtures by monitoring cross peaks by structural Analysis (various isomers), chemical analysis, materials (Amorphous materials in particular) and for separating and quantifying analytes in solution.

Characterizing heterogeneous samples with 2D lineshapes, such as, for example: polydisperse polymer samples, materials such as mixtures, blends, and emulsions in which the same molecule may experience different environments within spatially distinct regions of the sample (down to angstrom/nanometer scale).

The invention can be used to distinguish the environment of a molecule, for example, determining the contacts with other molecules does an analyte make. Heterogeneous samples can also be analyzed using preferred embodiments of the invention.

Analyzing bio-polymers can also be conducted in conjunction with thermodynamics, phase-transitions, conformational-transitions (for example: helix-coil transitions).

Preferred embodiments provide different methods for generating libraries in analysis such as the use a set of standards to separate overlapping contributions, identifying distinct cross peaks for a particular compound, identifying distinct cross peaks for contacts between two molecules, and the use lineshapes to distinguish the environment of a molecule.

Figure 7:
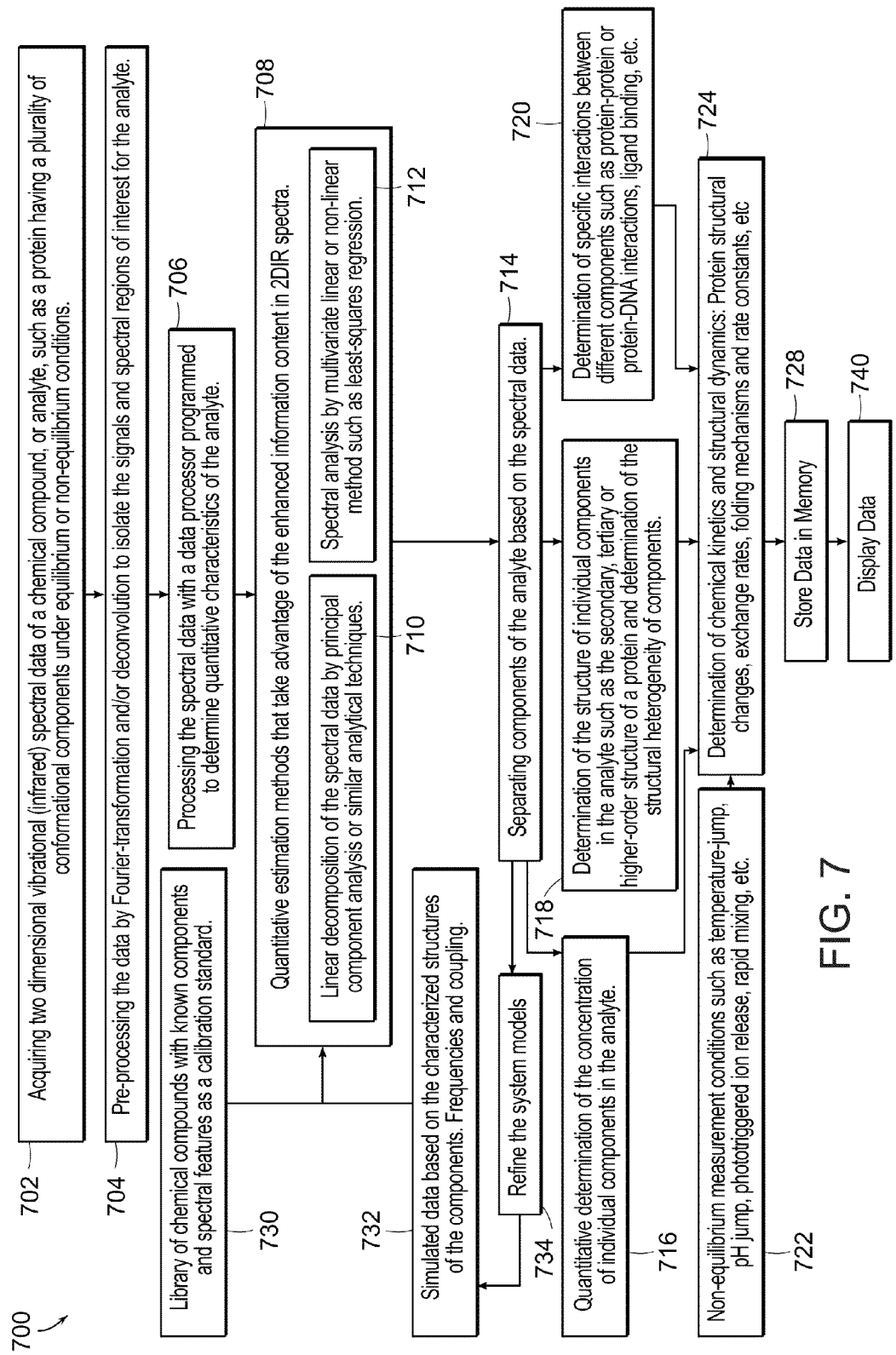
FIG. 7 illustrates a process sequence for obtaining and analyzing spectral data in accordance with preferred embodiments of the invention.

FIG. 7 illustrates a process sequence for determining quantitative characteristics of an analyte. The system shown in FIGS. 1A and 1B can be used to acquire spectral data that is analyzed 700 using a data processor or computer system to provide quantitative and structural characteristics of an analyte. After the acquisition 702 of 2D infrared data, the processing system performs a transformation or deconvolution 704 of the data to separate spectral features for the analyte. The spectral features can then be further processed 706 to provide quantitative characteristics of the analyte. This quantitative processing 708 can include methods for estimating or predicting certain characteristics using, for example, linear decomposition 710 of the spectral data by principal component analysis or other analytical techniques, or alternatively by using multivariate linear or non-linear methods 708, such as lease squares regression.

By separating 714 the individual components of the analyte using the spectral data and analytical processes, the concentration 716 of the components in the analyte can be determined. Additionally, the structure of these components can be determined 718 such as the secondary, tertiary or higher order structure. The interactions 720 between the components can also be determined, such as protein-protein or protein-DNA interactions or ligand binding can also be determined. Certain non-equilibrium measurement conditions 722 can also be used to temporally alter the analyte and thereby measure and determine 724 chemical kinetics and structural dynamics of the analyte. The resulting data can be stored in memory 728 and displayed on a display 740.

Additionally, in certain preferred embodiments a stored library of chemical compounds can be used to identify 730 spectral features and provide for calibration. Also, the analytical results 714 can be used to adjust the system model or process 734 and provide for the formation of simulated data 732 based on the identified structures, frequencies and coupling characteristics of a particular analyte.

Coherent two-dimensional infrared spectroscopy measures the correlation between vibrational frequencies. A cross peak is the result of exciting a given frequency ($\omega_1$) and stimulating emission from a different frequency ($\omega_2$). Cross peaks are only observed if two vibrations are connected by electrostatic interactions, or if vibrational energy transfer occurs following excitation. Since vibrational energy transfer only occurs over short ranges, a cross peak is observed only if two vibrations share common atoms or reside within the same chemical species. In solution, if two vibrations are due to two different species (molecules), no cross peaks are observed.

The term two-dimensional spectroscopy is also applied to a different (non-coherent) technique in which correlations between the intensities of peaks in a series of one-dimensional spectra are plotted on a second frequency axis. Spectra are collected as a function of an external variable such as temperature, concentration, or time. Peaks whose amplitudes have the same dependence on the external variable can have a high correlation factor, whereas peaks that are independent are not correlated, and thus do not exhibit cross peaks. Note that this method does not provide information on whether two vibrations arise from the same molecule, or from different species, as long as the concentration of the two species are correlated.

A preferred embodiment of the invention uses a coherent two-dimensional version of correlation spectroscopy: 2D/2D correlation spectroscopy. Instead of one-dimensional spectra, 2D infrared spectra are obtained and the correlation coefficient between a pair of [$\omega_1$ $\omega_3$] frequencies and all other [$\omega_1$ $\omega_3$] frequencies within the series of spectra can be represented, processed and recorded. The set of spectra is derived from the set of sixteen proteins used in the previous structural analysis (see FIG. 8). Note that since the correlation coefficient is independent of the order of [x,y] pairs, it is not necessary to sort the protein spectra in order to calculate the correlation coefficients. In order to plot the correlation coefficients between all [$\omega_1$ $\omega_3$] pairs in our set of spectra, a four-dimensional plot is needed. Instead, by fixing the first set of frequencies and plotting the correlation of this set with other frequency pairs in the series.

Figure 8:
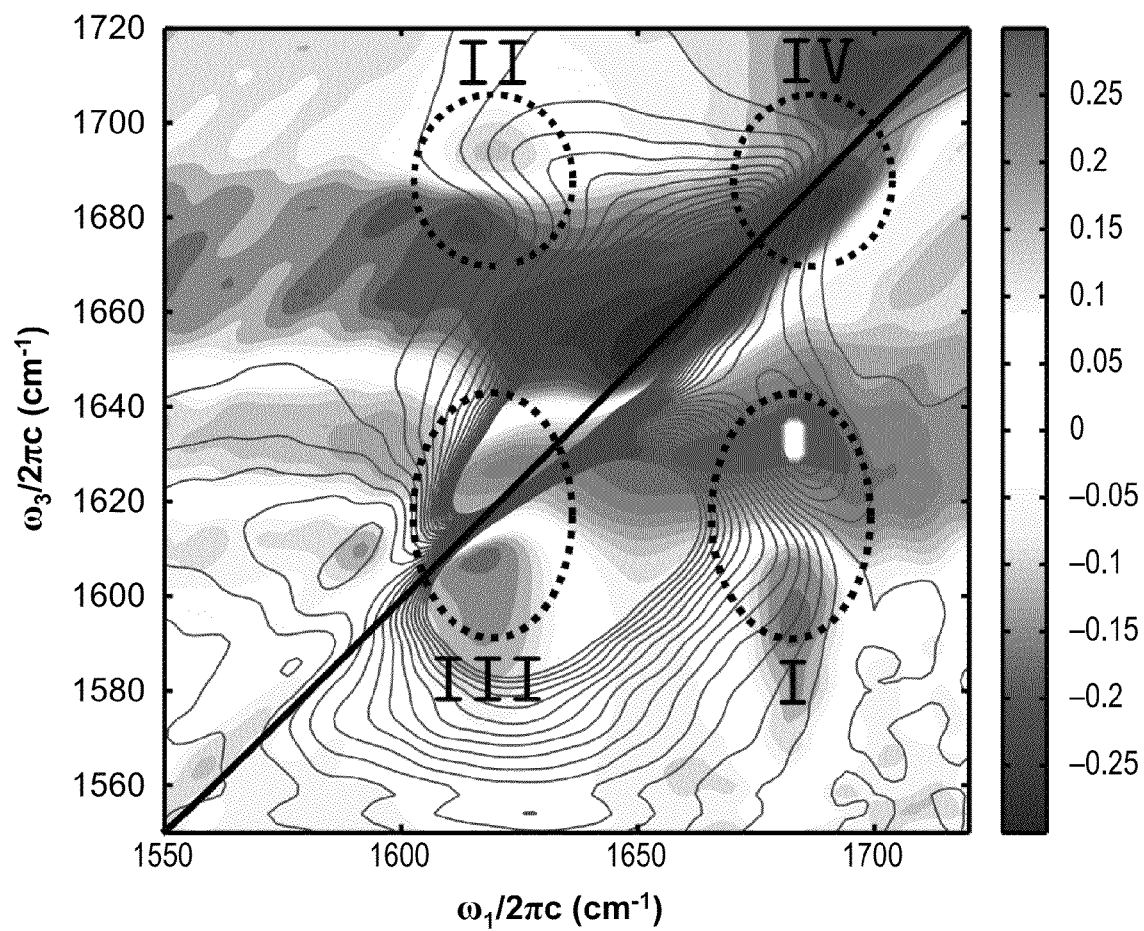
FIG. 8 is a 2D spectrum illustrating the correlation coefficient to indicate connections between conformations.

FIG. 8 shows the correlation coefficient between [$\omega_1$ $\omega_3$]= [1684 1634] cm$^{-1}$ (labeled I) and all other pairs of frequencies in the spectrum. The amplitude of the correlation coefficient is represented on the color axis. Solid contours correspond to a single spectrum of a mostly beta-sheet protein, immunoglobulin-G overlaid for reference. The white square represents the frequencies [1684 1634] cm$^{-1}$ used as the reference point for the correlation coefficients. This set of frequencies is chosen because it corresponds to a cross peak between the two main transitions in beta sheets. FIG. 8 shows that the [1684 1634] cm$^{-1}$ is correlated with its mirror peak above the diagonal near [1634 1684] cm$^{-1}$ (FIG. 8, labeled II) this is due to the fact that the two cross peaks are related to the two transitions in beta-sheet, so for proteins that have a higher beta-sheet content, the two peaks will carry more amplitude than for alpha-helical proteins, and thus the amplitude of these two peaks is correlated across the set. A similar interpretation can be made for the correlation between the cross peak and the two diagonal peaks (labeled III and IV). Also, note that each cross peak in the 2D/2D correlation spectrum appears as a positive/negative doublet along the detection axis. This is the result of vibrational anharmonicity and it mirrors the spectrum as a whole. Also note that despite the broad and featureless peaks observed in the spectra the 2D/2D correlation peaks, particularly the cross peaks are isolated and well resolved.

In general, 2D/2D correlation spectroscopy is an intuitive method for isolating diagonals and cross peaks arising from particular structures (or analytes) in mixtures, even when the spectra are broad or highly congested. More importantly, the described analysis method can be used in order to assign spectral features of individual components in a chemical mixture.

Additional examples of structural information contained in 2D infrared spectra are illustrated in connection with FIG. 9A in which aptamers are used to bind to specific molecules which can then be measured to obtain 2D infrared spectra. Cross peaks (i.e. off diagonal spectral components) can be used to identify and separate conformational components using the systems and methods described herein.

Figures 9A, 9B:
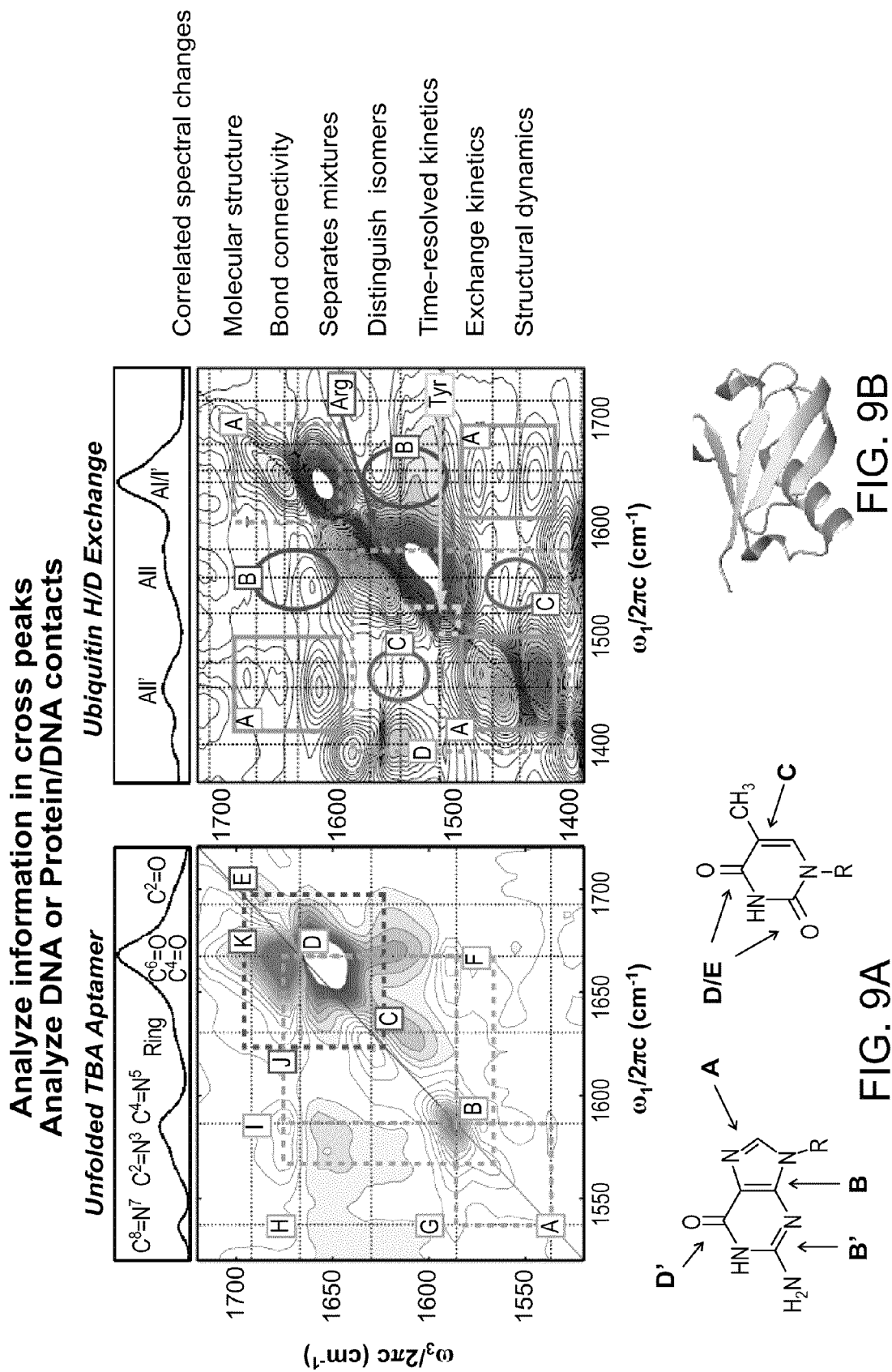
FIG. 9A illustrates a more detailed analysis of cross peaks of DNA spectral data in accordance with preferred embodiments of the invention in which specific spectral features are labeled for an unfolded TBA aptamer.
FIG. 9B graphically illustrates spectral cross peaks to identify and characterize ubiquitan hydrogen/deuterium (H/D) exchange in a sample.

FIG. 9A shows the 2D spectrum of a short single-stranded DNA polymer, thrombin binding aptamer (TBA), in its unfolded form. As shown, the diagonal peaks can be assigned to specific vibrations of the deoxy-guanosine (peaks A,B,B' and D') and deoxy-thymine (peaks D, C and E) bases that compose TBA, and the cross peaks indicate report on the three-dimensional structure of the DNA polymer. The two-dimensional spectrum can be used to measure the conformation of the DNA in solution as well as the conformational changes associated with protein binding.

FIG. 9B illustrates an example in which hydrogen/deuterium exchange 2D infrared spectroscopy on Amide-I and Amide-II/II' vibrations is used to assess the conformational flexibility and solvent exposure of secondary structures in ubiquitin. Amide-II vibrations centered near 1550 $cm^{-1}$ undergo a 100 $cm^{-1}$ frequency shift upon deuteration. In this example, protonated ubiquitin is dissolved in $D_2O$. Residues that are exposed to the solvent undergo rapid H/D exchange whereas residues that are buried within the core of the protein remain protonated. The cross peaks between Amide-II with Amide-I vibrations indicate the secondary structure of those residues that have not undergone exchange, and similarly the cross peaks between Amide-II' and Amide-I contain information on the structure of the residues which are more exposed to the solvent. In the current example it is observed that residues in the alpha-helix portion of ubiquitin undergo slow exchange whereas the beta-sheet exchanges more rapidly. Spectra measured as a function of time following reconstitution of the protein in $D_2O$, give direct information on the kinetics of H/D exchange, such as the rate of exchange (reaction) which can be directly related to the structural dynamics of the secondary structures within the protein.

Figures 10A, 10B, 10C:
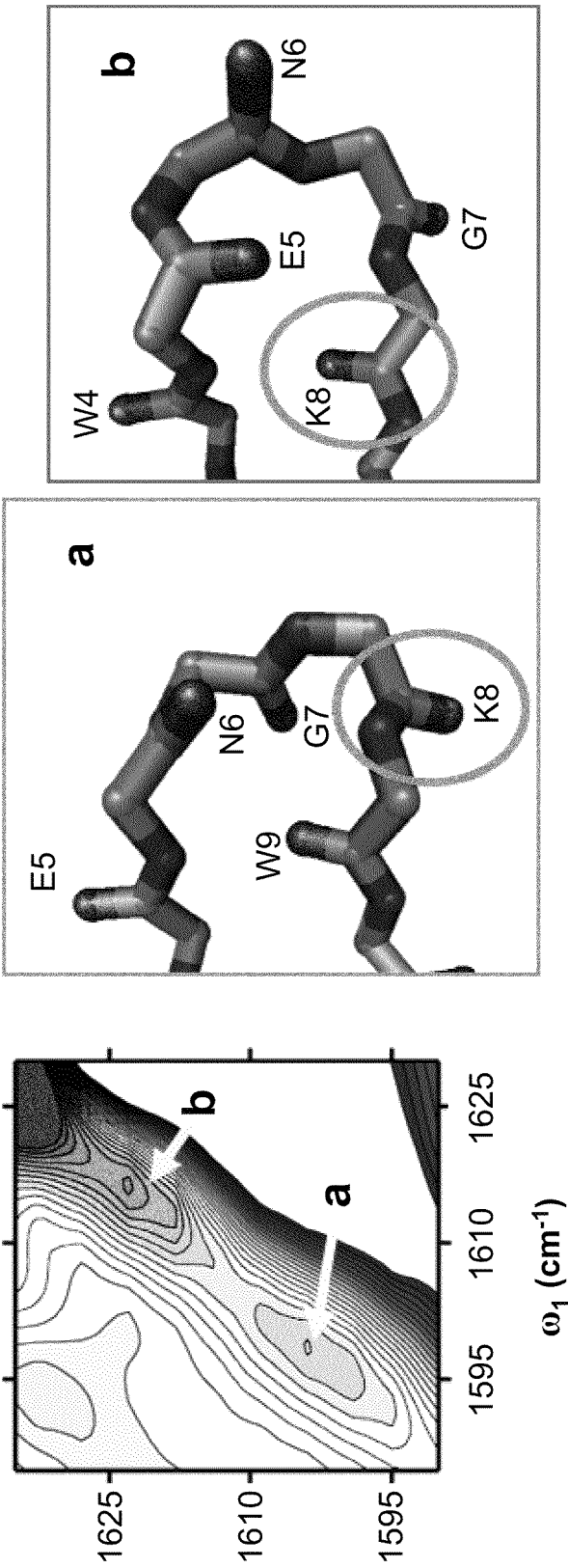
FIGS. 10A-10E illustrate the use of isotope labeling to distinguish among folded, frayed, disorder, extended disorder and bugled turn conformations.
Figure 10D:
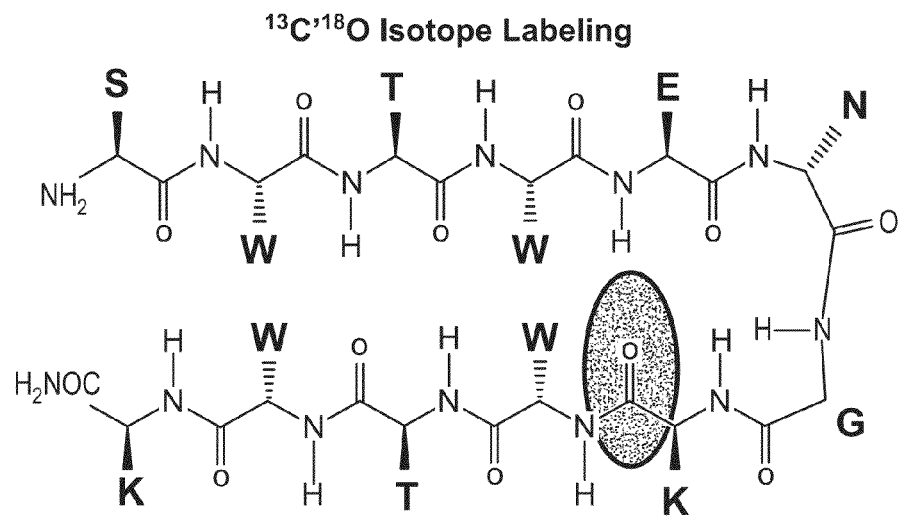
Figure 10E:
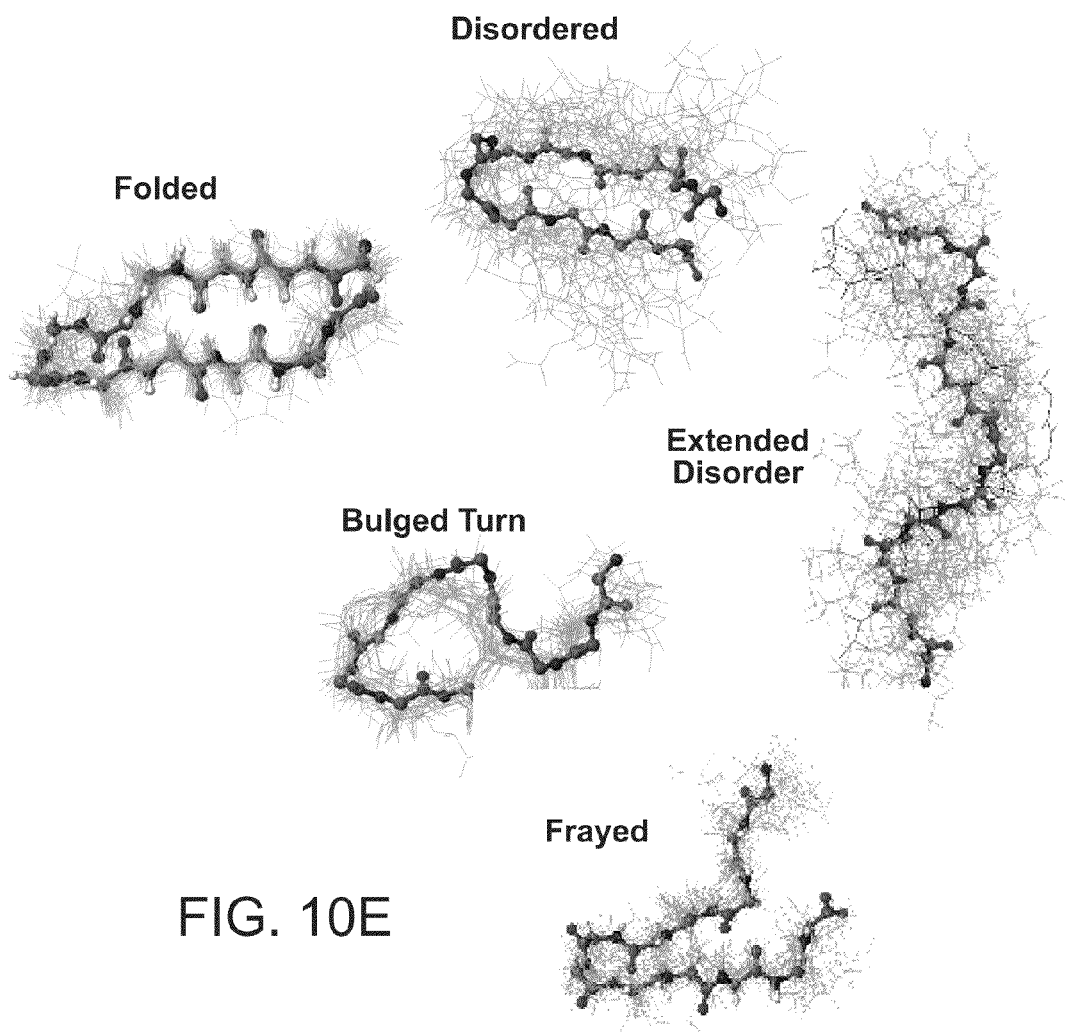

FIGS. 10A-10E illustrate the use of isotope labeling to identify and quantify distribution of conformers in an analyte. Isotope labels serve to de-couple and localize a single residue from the delocalized excitonic vibrations of the peptide backbone, providing an isolated probe of the structure and dynamics. The example depicted shows the structures of the main conformers of the tryptophan zipper 2 peptide (TrpZip2). The peaks labeled (a,b) in the spectrum (FIG. 10A) arise from a single $^{13}C=^{18}O$ Cisotope lablel K8, and are assigned to two different conformations of the beta-turn as shown in FIGS. 10B and 10C. In the present example, the two conformations exchange on the sub-millisecond timescale, and since most analytical techniques cannot measure conformational changes on this short timescale, an "averaged-out" conformation is measured instead. This particular example highlights the enhanced structural content and fine time resolution available with 2D infrared spectroscopy. Similarly, different isotope labels enable separation and the determination of the structure and concentration of specific conformers as shown in FIG. 10E.

Figure 11C:
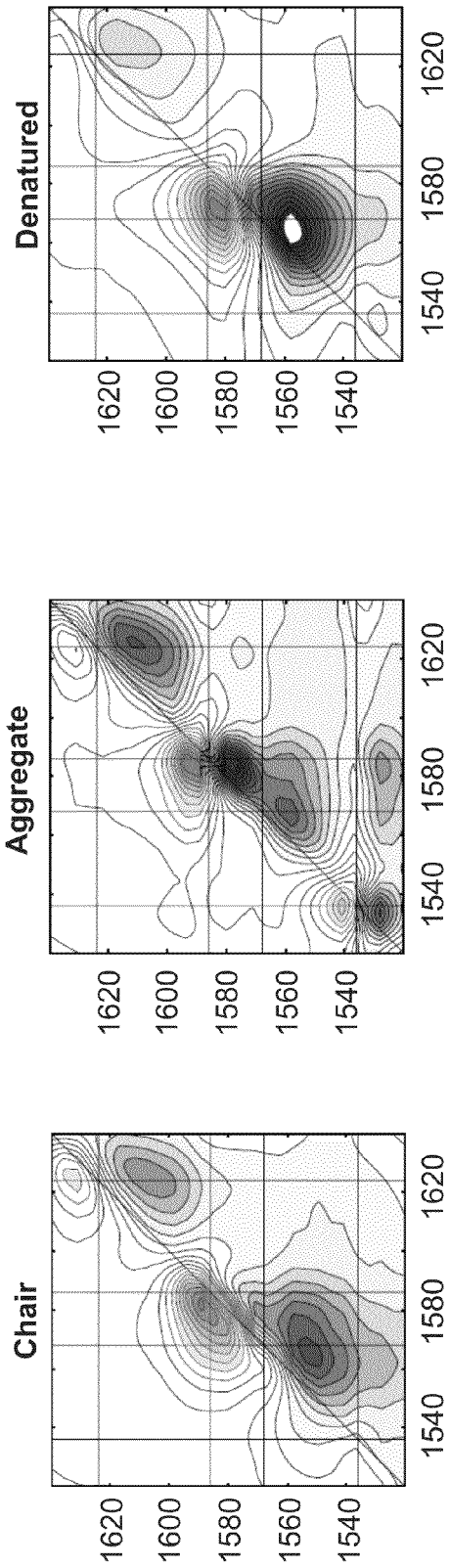
FIGS. 11A-11C illustrate method for analyzing DNA or RNA structures using aptamers which preferentially bind to target molecules.
Figure 11C:
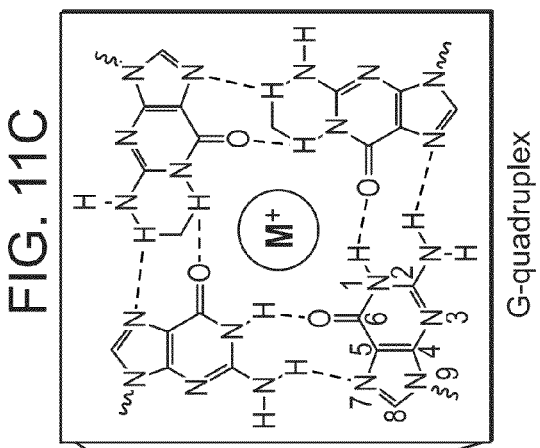
Figure 11B:
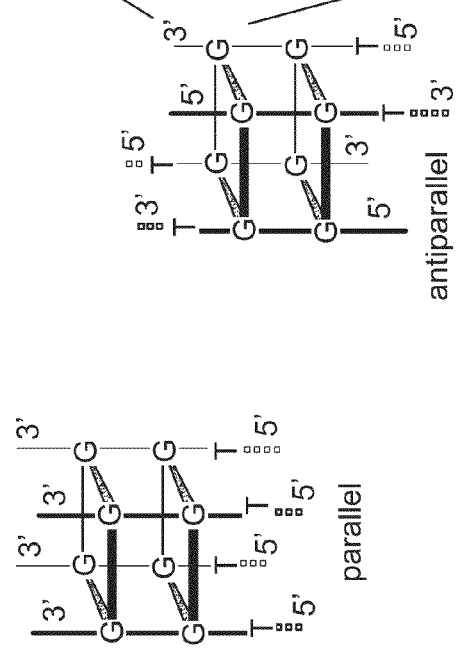
Figure 11A:
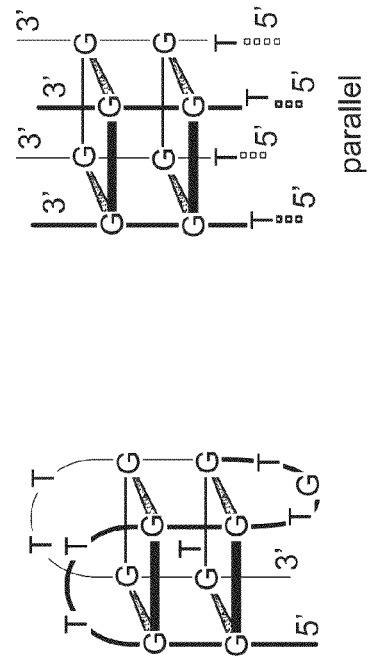

Illustrated in FIGS. 11A-11C are spectra corresponding to three different structures of the thrombin binding aptamer (TBA): chair conformation (folded), denatured (unfolded), and aggregate. The diagonal and off-diagonal peaks are very distinct for all three conformations. Similar to the example depicted in FIG. 9A, this example shows how the diagonal and off-diagonal peaks can be used to measure the molecular structure of DNA and quantify the populations of the different conformers in solution. In addition to molecular structure, 2D infrared measurements can characterize supra-molecular structure, such as the long-range order present in TBA aggregates.

Figure 12:
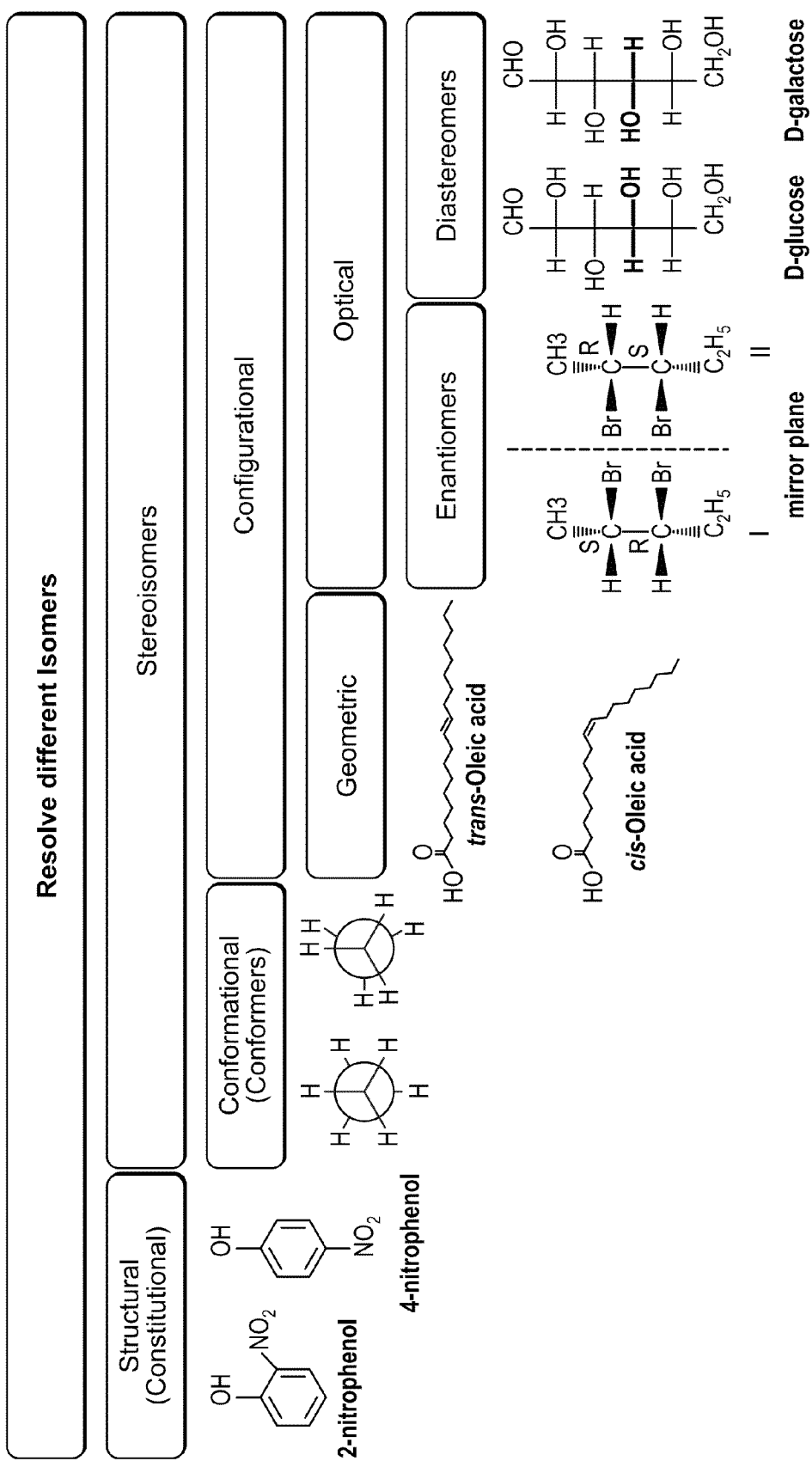
FIG. 12 summarizes methods for resolving different isomers including structural, conformational, geometric and optical features.

FIG. 12 illustrates generally the use of 2D infrared spectral analysis to detect and characterize different isomers contained in one or more analytes. The basic structural differentiation of stereoisomers, the separation of different conformers and geometries and different optical characteristics enantiomers/diastereomers can also be determined. Different bond conformations also have different vibrational spectra even where mass and/or chemical composition is identical.

Figure 13:
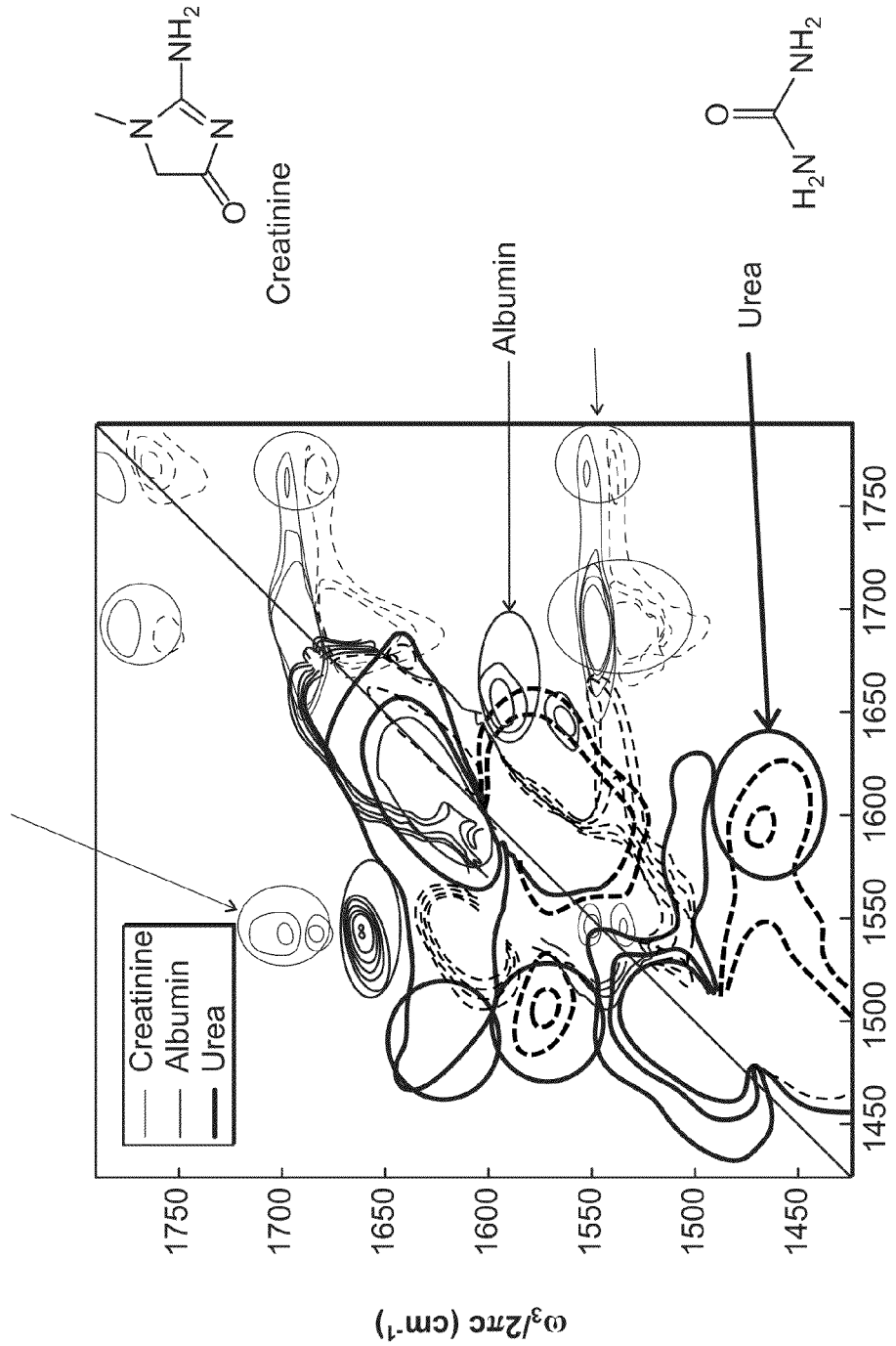
FIG. 13 illustrates a 2D infrared analysis of blood analytes.

Illustrated in FIG. 13 is the application of 2D infrared to the quantitation of compounds commonly found in blood samples: creatinine, albumin, and urea. The three molecules have multiple overlapping peaks in the 1450-1750 $cm^{-1}$ region of the spectrum, and thus produce a very congested absorption spectrum (diagonal), however the cross peaks, which appear only when two vibrations correspond to the same species, are better isolated. These cross peaks can be integrated to extract the concentrations of individual analytes in blood-samples or similar chemical mixtures.

Figure 14:
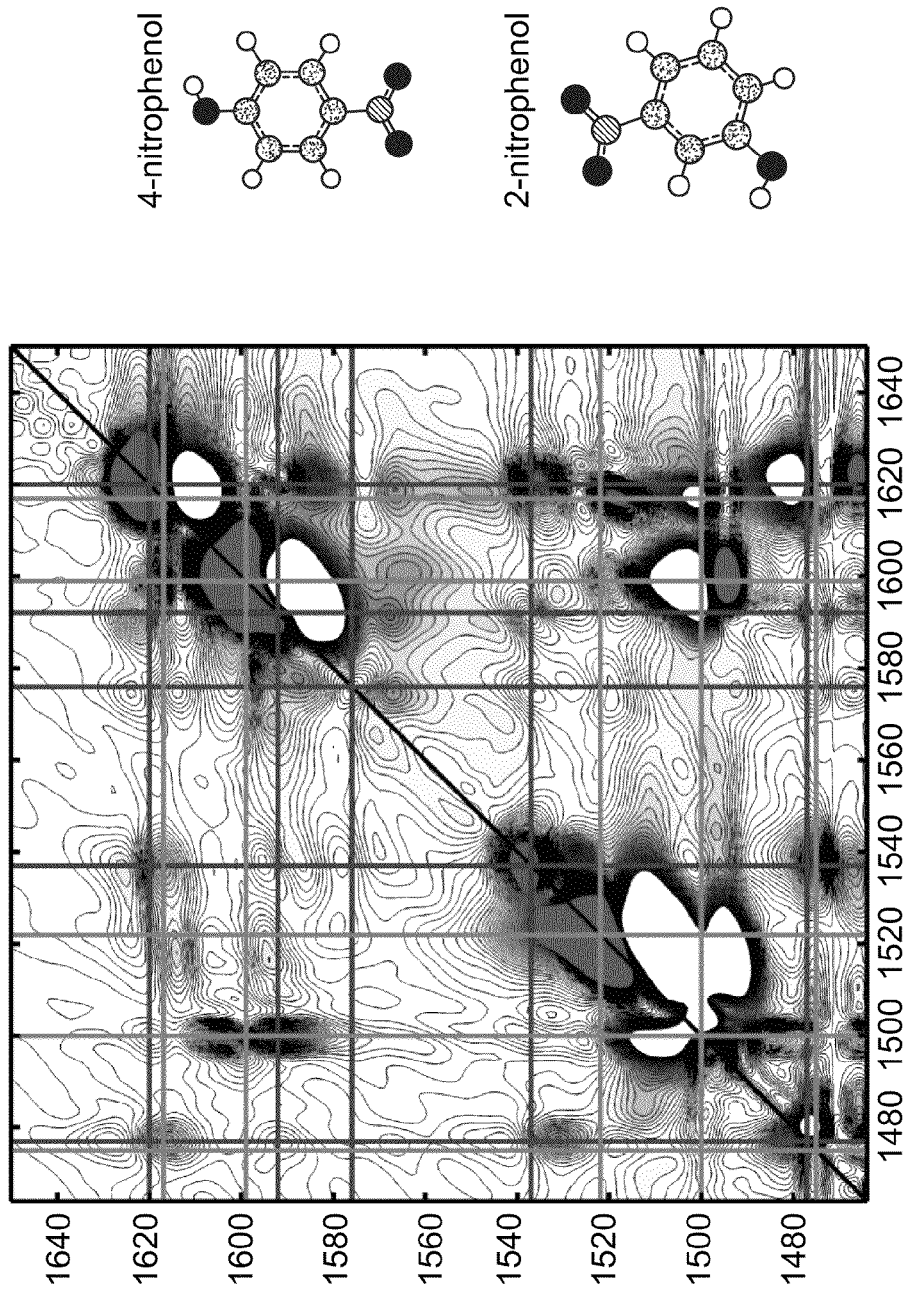
FIG. 14 illustrates the resolution of components in isomeric mixtures, such as nitrophenols.

Shown in FIG. 14 is a method of resolving isomeric mixtures, in this example the spectrum of a 50:50 mixture of two structural isomers of nitrophenol (2-nitrophenol and 4-nitrophenol) is depicted as an illustration of how cross peaks in the spectrum can be used to perform a "spectroscopic separation" to identify and quantify each component in the mixture. Similar chemical properties make structural isomers particularly difficult to separate with conventional analytical methods. Most importantly, 2D infrared spectroscopy can be used to identify isomers which are rapidly interconverting in solution. Conformational isomers in particular, which are only differentiated by a rotation around a single bond, can interconvert in the picosecond to millisecond timescale. These isomers are difficult to separate using conventional techniques (such as chromatography), since a single isomer can interconvert back to an equilibrium mixture in a few milliseconds.

Figure 15A:
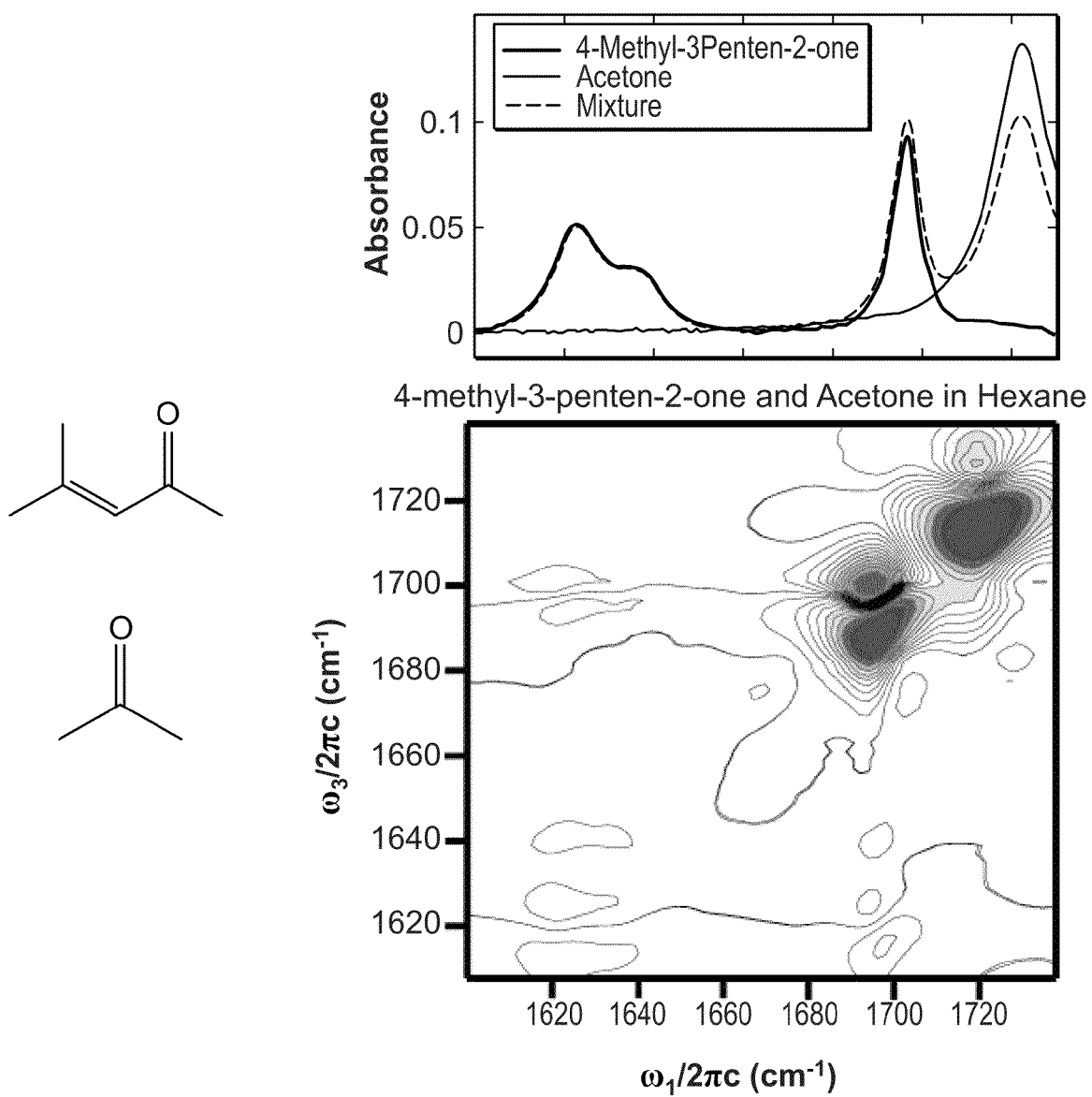
FIGS. 15A and 15B illustrate the use of cross peak analysis to separate mixtures.
Figure 15B:
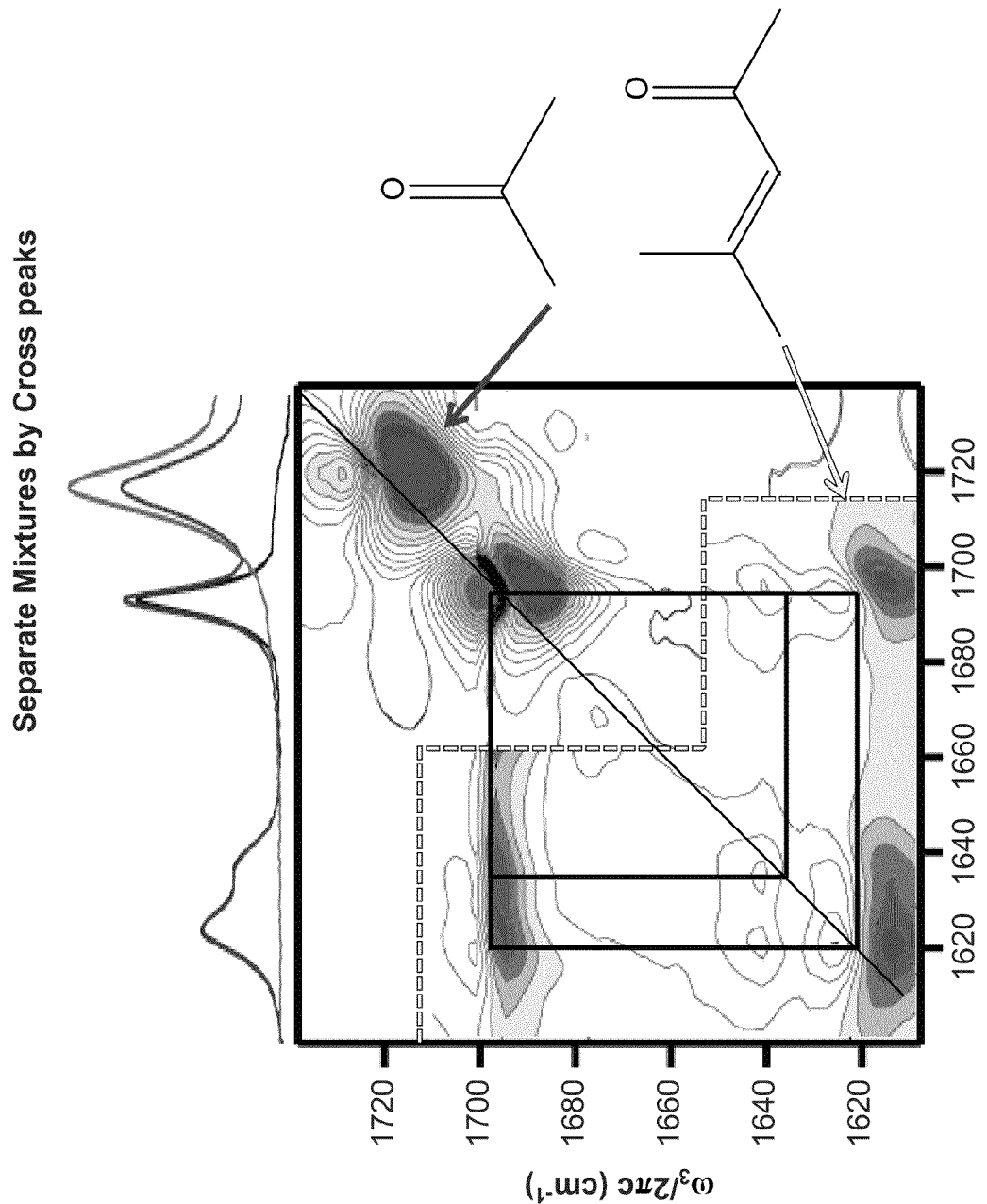

Shown in FIGS. 15A and 15B is an illustration of the methods of using cross peaks to separate components of mixtures in this example, a mixture of organic compounds, such as acetone and hexane.

While the present invention has been described here in conjunction with a preferred embodiment, a person with ordinary skill in the art, after reading the foregoing specification, can effect changes, substitutions of equivalents and other types of alterations to the system and method that are set forth herein. Each embodiment described above can also have included or incorporated therewith such variations as disclosed in regard to any or all of the other embodiments. Thus, it is intended that protection granted by Letters Patent hereon be limited in breadth only by definitions contained in the appended claims and any equivalents thereof.

What is claimed is:

1. A method for measuring a conformational structure of an analyte comprising:
   processing two-dimensional spectral data of an analyte with a data processor to determine a plurality of conformational components of the analyte in a sample, the analyte comprising at least one protein having a plurality of residues, and wherein the spectral data includes amplitude and phase of a signal emitted by the analyte in response to a plurality of incident light pulses;
   determining, with the data processor, a first quantitative value of a first conformational component of the analyte, the first quantitative value including a first fraction of a first residue for the first conformational component; and
   determining, with the data processor, a second quantitative value of a second conformational component of the analyte, the second quantitative value including a second fraction of the first residue for the second conformational component.

2. The method of claim 1 further comprising determining a concentration of the first conformational component.

3. The method of claim 1 further comprising detecting two dimensional infrared spectral data of a sample containing the analyte.

4. The method of claim 3 wherein the step of detecting spectral data comprises illuminating the sample with a plurality of infrared wavelengths and detecting a plurality of wavelengths with a detector.

5. The method of claim 1 further comprising processing the spectral data with a data processor.

6. The method of claim 1 wherein the step of determining the first quantitative value provides a relative percentage of the first conformational component.

7. The method of claim 1 wherein the analyte comprises a protein.

8. The method of claim 1 further comprising using a label to identify a conformational structure of the analyte.

9. The method of claim 1 wherein the processing step comprises separating components of the analyte using spectral cross peaks.

10. The method of claim 1 further comprising performing a linear decomposition of the spectral data.

11. The method of claim 1 further comprising determining secondary, tertiary or higher order components of the analyte.

12. The method of claim 1 further comprising detecting time varying infrared spectral data.

13. The method of claim 7 further comprising determining a concentration of an a-helix conformation.

14. The method of claim 7 further comprising determining a concentration of a β-sheet conformation.

15. The method of claim 1 further using electronically stored data to determine a conformer in the analyte.

16. The method of claim 1 further comprising displaying two dimensional vibrational spectra on a display.

17. The method of claim 1 further comprising determining a size of a component in the sample.

18. The method of claim 1 further comprising determining a correlation coefficient of the sample.

19. The method of claim 1 further comprising illuminating the sample with at least four non-colinear beams of light generated with a first laser source and a second laser source pulse that is temporarily synchronized with the first laser source.

20. The method of claim 1, wherein the two dimensional spectral data includes a two dimensional plot of excitation frequency versus detection frequency.

21. The method of claim 20, further comprising identifying common residues based on cross peaks in the two dimensional plot.

22. The method of claim 1, wherein the two dimensional spectral data is generated using at least a pair of infrared pulses optically coupled to the analyte and a further pulse to stimulate an emitted signal.

23. The method of claim 22, wherein the emitted signal is detected in the frequency domain using a grating spectometer.

24. The method of claim 1, wherein the two dimensional spectral data is generated using a pair of excitation pulses delayed in time and measuring a signal spectrum as a function of the time delay between the excitation pulses.

25. The method of claim 24, wherein the processing of the two dimensional spectral data further comprises performing a Fourier transform along the excitation time delay to obtain excitation frequency.

26. The method claim 1, wherein the two dimensional spectral data is derived by measuring both amplitude and phase of an emitted electric field from the sample.

27. The method of claim 26, wherein the measuring the amplitude and phase of the emitted electric field includes utilizing an external reference beam or utilizing an internal reference pulse.

28. The method of claim 1, wherein the two dimensional spectral data is derived utilizing a pair of non-colinearly focused excitation pulses and overlapping an emitted signal with an external reference pulse.

29. The method of claim 1, wherein the two dimensional spectral data includes excitation frequency versus detection frequency, excitation time versus detection frequency, excitation frequency versus detection time, or excitation time versus detection time.

30. The method of claim 1, further comprising determining a ratio of a first isomer to a second isomer in the analyte.

31. The method of claim 1 further comprising adjusting a temperature of the sample.

32. The method of claim 31 further comprising using a T jump laser to adjust the temperature of the sample to measure spectral data at different temperatures.

33. A system for measuring vibrational spectral data of an analyte comprising:
   a light source system that provides illuminating light pulses at a plurality of wavelengths;
   an optical system that delivers the illuminating light pulses onto an analyte;
   a detector system that detects light from the analyte to provide spectral data including amplitude and phase of the detected light from the analyte, the analyte comprising at least one protein having a plurality of residues including a first residue; and
   a data processing system that processes two dimensional amplitude and phase spectral data of the analyte to determine a first fraction of the first residue of a first conformational component of the analyte and a second fraction of the first residue of a second conformational component of the analyte.

34. The system of claim 33 further comprising a computer program that determines a concentration of a conformational component.

35. The system of claim 33 further comprising a two dimensional detector array that detects two dimensional infrared spectral data of a sample containing the analyte.

36. The system of claim 33 further comprising a computer program that determines the quantitative characteristic and determines a relative percentage of the conformational component.

37. The system of claim 33 wherein the analyte comprises a protein.

38. The system of claim 33 further comprising a label to identify a conformational structure of the analyte.

39. The system of claim 33 wherein the system detects spectral data wherein the sample is illuminated with a plurality of infrared wavelengths and the detection system detect a plurality of wavelengths with a detection.

40. The system of claim 33 wherein the processing separates components of the analyte using spectral cross peaks.

41. The system of claim 33 wherein the processing system performs a linear decomposition of the spectral data.

42. The system of claim 33, wherein the two dimensional spectral data comprises an excitation frequency dimension and a detection frequency dimension.

43. The system of claim 42, wherein the data processor identifies common residues based on cross peaks in the two dimensional data.

44. The system of claim 33, wherein the light source system generates a pair of infrared pulses to illuminate the analyte and a third pulse to illuminate an emitted signal.

45. The system of claim 44, wherein the emitted signal is detected in the frequency domain using a grating spectometer.

46. The system of claim 33, wherein the two dimensional spectral data is derived using a pair of excitation pulses delayed in time and measuring a signal spectrum as a function of the excitation time delay between the excitation pulses.

47. The system of claim 46, wherein the derived two dimensional spectral data further comprises Fourier transformed spectral data along the excitation time delay to obtain excitation frequency.

48. The system claim 33, wherein the two dimensional spectral data is generated by detecting amplitude and phase of an electric field received from the analyte.

49. The system of claim 48, wherein the detector system detects amplitude and phase of the electric field by utilizing an external reference beam or utilizing an internal reference pulse.

50. The system of claim 33, wherein the two dimensional spectral data is derived utilizing a pair of non-collinearly focused excitation pulses and overlapping an emitted signal with an external reference pulse.

51. The system of claim 33, wherein the two dimensional spectral data includes excitation frequency versus detection frequency, excitation time versus detection frequency, excitation frequency versus detection time, or excitation time versus detection time.

52. The method of claim 33, wherein the light source system generates a plurality of temporally displaced light pulses.

53. The system of claim 52, wherein a first pulse is colinear with a second pulse.

54. The system of claim 52 wherein a first pulse is non colinear with a second pulse.

55. The system of claim 52, wherein the light source system generates at least a first pulse, a second pulse and a third pulse.

56. The system of claim 33, further comprising a plurality of non colinear beams including a beam split to form a local oscillator and a tracer.

57. The system of claim 33 further comprising a temperature controller to adjust the temperature of the analyte to detect spectral data at a plurality of different temperatures.

58. A method for measuring a conformational change of an analyte component comprising:
    detecting two dimensional spectral data of an analyte to determine a characteristic of a conformational component of the analyte, the spectral data including amplitude and phase of detected light from the analyte;
    processing the spectral data with a data processor to determine a first quantitative value of a conformational component of the analyte; and subsequently, after a change in a concentration in the conformational component,
    determining a second quantitative value of the conformational component of the analyte.

59. The method of claim 58 further comprising determining a concentration of the first conformational component.

60. The method of claim 58, further comprising detecting two dimensional infrared spectral data of a sample containing the analyte.

61. The method of claim 60 wherein the step of detecting spectral data comprises illuminating the sample with a plurality of infrared wavelengths and detecting a plurality of wavelengths with a detector.

62. The method of claim 58, further comprising processing the spectral data including a first polarization component and a second polarization component with the data processor.

63. The method of claim 58 wherein the step of determining the first quantitative value provides a relative percentage of the first conformational component.

64. The method of claim 58 wherein the analyte comprises a protein having a plurality of residues, the method further comprising determining a fraction of one of the plurality of residues to determine the first quantitative value and subsequently determining a second fraction of said one of the plurality of residues after the change in concentration.

65. The method of claim 64 further comprising determining a concentration of an a-helix conformation.

66. The method of claim 64 further comprising determining a concentration of a β-sheet conformation.

67. The method of claim 58 further comprising using a label to identify a conformational structure of the analyte.

68. The method of claim 58 wherein the processing step comprises separating components of the analyte using spectral cross peaks.

69. The method of claim 58 further comprising performing a linear decomposition of the spectral data.

70. The method of claim 58 further comprising determining secondary, tertiary or higher order components of the analyte.

71. The method of claim 58 further comprising detecting time varying spectral data.

72. The method of claim 58 further using electronically stored data to determine a conformational component in the analyte.

73. The method of claim 58 further comprising displaying two dimensional vibrational spectra on a display.

74. The method of claim 58 further comprising determining a size of a component in a sample.

75. The method of claim 58 further comprising determining a correlation coefficient of a sample.

76. The method of claim 58 further comprising illuminating the sample with at least four non-colinear beams of light and a second laser source pulse.

77. The method of claim 58 further comprising processing spectral data of a blood analyte.

78. The method of claim 58 further comprising performing a nonlinear decomposition of the spectral data.

79. The method of claim 58 further comprising controlling delays in an optical system that couples a light source system to a sample containing the analyte.

80. The method of claim 79 wherein the controlling step comprises adjusting one or more notarized stages.

81. The method of claim 58 further comprising controlling a polarization of one or more beam paths coupled to a sample containing the analyte.

82. The method of claim 58 further comprising detecting a reflected third order signal and a local oscillator beam on a stripe of a detector and detecting a second pair of pulses with a further stripe of the detector.

83. The method of claim 58 further comprising processing data using singular value decomposition.

84. The method of claim 58 further comprising adjusting a temperature of the analyte to obtain spectral data at different temperatures.

85. The method of claim 58 further comprising using a laser to control a temperature of the analyte.

* * * * *